United States Patent
Goto et al.

(10) Patent No.: US 9,042,616 B2
(45) Date of Patent: May 26, 2015

(54) MEDICAL IMAGE PROCESSING DEVICE

(75) Inventors: Tomoaki Goto, Ichikawa (JP); Tetsutaro Ono, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 69 days.

(21) Appl. No.: 13/991,012

(22) PCT Filed: Dec. 1, 2011

(86) PCT No.: PCT/JP2011/077761
§ 371 (c)(1),
(2), (4) Date: May 31, 2013

(87) PCT Pub. No.: WO2012/074039
PCT Pub. Date: Jun. 7, 2012

(65) Prior Publication Data
US 2013/0251231 A1 Sep. 26, 2013

(30) Foreign Application Priority Data
Dec. 2, 2010 (JP) ................................ 2010-269073

(51) Int. Cl.
*G06K 9/00* (2006.01)
*G06T 7/00* (2006.01)
*A61B 5/055* (2006.01)

(52) U.S. Cl.
CPC .............. *G06T 7/0012* (2013.01); *A61B 5/055* (2013.01); *G06T 2207/30016* (2013.01)

(58) Field of Classification Search
USPC .......... 382/100, 128, 130, 131, 132; 128/922; 348/4–27; 250/336.1, 338.2, 363.04
See application file for complete search history.

(56) References Cited

U.S. PATENT DOCUMENTS 6,161,031 A * 12/2000 Hochman et al. ............. 600/407
8,750,584 B2 * 6/2014 Matsuba et al. .............. 382/128
(Continued)

FOREIGN PATENT DOCUMENTS

JP   A-7-320028    12/1995
JP   A-11-507565   7/1999
(Continued)

OTHER PUBLICATIONS

Hirata et al., "Voxel-Based Morphometry to Discriminate Early Alzheimer's Disease from Controls," *Neuroscience Letters*, 2005, vol. 382, pp. 269-274.
(Continued)

*Primary Examiner* — Anand Bhatnagar
(74) *Attorney, Agent, or Firm* — Oliff PLC

(57) ABSTRACT

Provided is a medical image processing device capable of determining a state of an obtained brain image and adjusting the obtained image to suit for performing tissue separation processing. The medical image processing device is configured to select a slice image to be processed as a target slice image from a brain image configured by a plurality of slice images, performs processing for measuring an effective maximum value in the cerebral parenchyma, an effective maximum value in a whole image, and a peak average value around the skull with respect to the selected target slice to determine necessity of high-signal-value-control processing based on the measured effective maximum value in the cerebral parenchyma, the effective maximum value in a whole image, and the peak average value around the skull so that when it is determined that the high-signal-value-control processing is necessary, the high-signal-value-control processing is performed to the brain image.

10 Claims, 18 Drawing Sheets

(56) References Cited

U.S. PATENT DOCUMENTS

| | | | |
|---|---|---|---|
| 8,768,431 B2* | 7/2014 | Ross et al. | 600/410 |
| 2006/0177115 A1* | 8/2006 | Fujita et al. | 382/128 |
| 2009/0221901 A1* | 9/2009 | Yamamoto et al. | 600/410 |
| 2009/0326360 A1* | 12/2009 | Baillet et al. | 600/410 |
| 2012/0195485 A1* | 8/2012 | Matsuba et al. | 382/131 |

FOREIGN PATENT DOCUMENTS

| | | |
|---|---|---|
| JP | A-2005-237441 | 9/2005 |
| JP | A-2007-68852 | 3/2007 |
| WO | WO 2007/023522 A1 | 3/2007 |

OTHER PUBLICATIONS

Bookstein, "'Voxel-Based Morphometry' Should Not Be Used with Imperfectly Registered Images," *NeuroImage*, 2001, vol. 14, No. 6, pp. 1-9.

Ashburner et al., "Unified Segmentation," *NeuroImage*, 2005, vol. 26, pp. 839-851.

Ashburner, "A Fast Diffeomorphic Image Registration Algorithm," *NeuroImage*, 2007, vol. 38, pp. 95-113.

Matsuda et al., "Statistical Analysis of SPECT, Image Diagnosis of Alzheimer's Dementia," *Medical View Co., Ltd.*, 2001, pp. 76-86.

International Search Report issued in International Patent Application No. PCT/JP2011/077761 dated Feb. 28, 2012.

* cited by examiner

FIG.7
(A) PROFILE PLOT (SIGNAL VALUES ON LINE SEGMENTS)
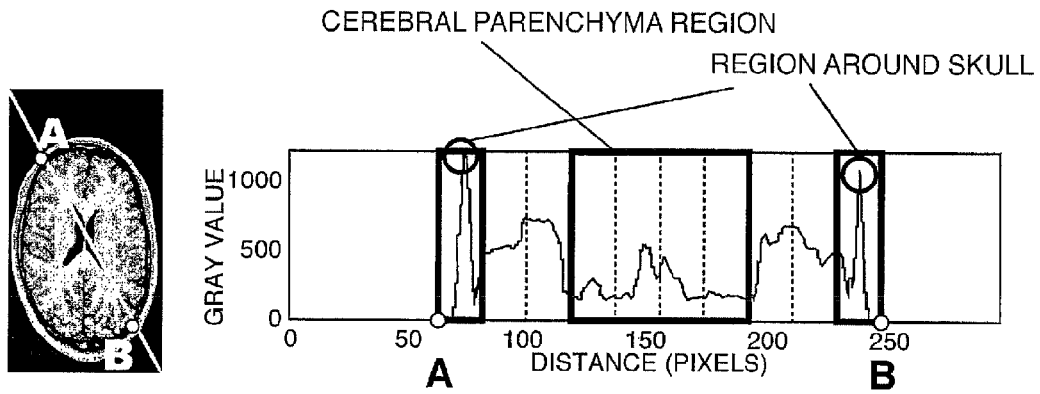
SIGNAL VALUE DISTRIBUTION BETWEEN A AND B
IS DIVIDED INTO 10 REGIONS
 4 REGIONS AT CENTER / CEREBRAL PARENCHYMA REGION
 2 REGIONS AT BOTH ENDS / REGION AROUND SKULL
(B)
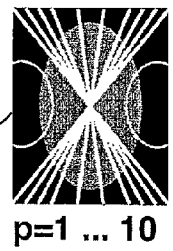
p=1 ... 10
NOT INCLUDED BECAUSE
ARTIFACT IS FREQUENTLY
INCLUDED
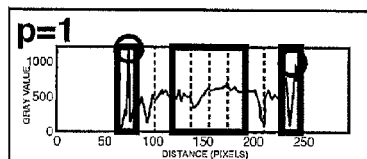
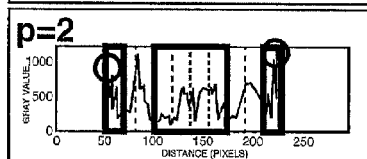
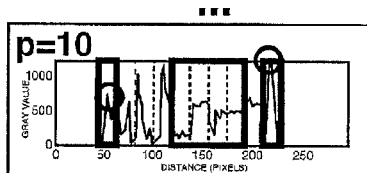

FIG.8

CALCULATION OF EFFECTIVE MAXIMUM VALUE OF CEREBRAL PARENCHYMA AND PEAK AVERAGE VALUE OF REGION AROUND SKULL (a) 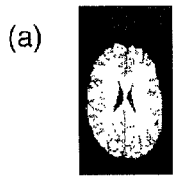  (b) 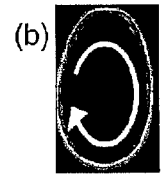

EFFECTIVE MAXIMUM VALUE OF CEREBRAL PARENCHYMA

PEAK AVERAGE VALUE OF REGION AROUND SKULL

 

HISTOGRAM OF CEREBRAL PARENCHYMA REGION OF ALL PLOTS

AVERAGING CUMULATED MAXIMUM VALUES FROM REGION AROUND SKULL OF ALL PLOTS

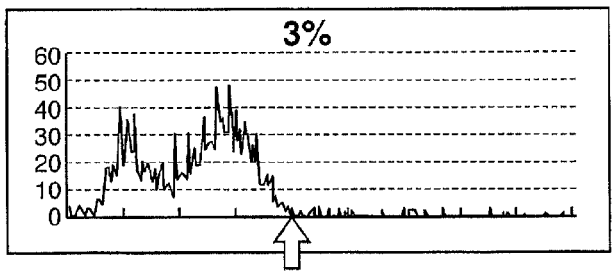

MAXIMUM VALUE WHEN EXCLUDING TOP 3 %
(EXCLUDING INFLUENCE OF HIGH SIGNAL ARTIFACT)

COMPARISON OF STRATIFIED TEMPLATES

FIG.13
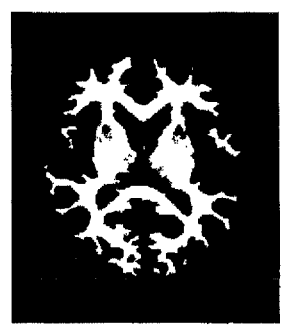
WHITE MATTER IMAGE
SPATIAL NORMALIZATION
SMOOTHING
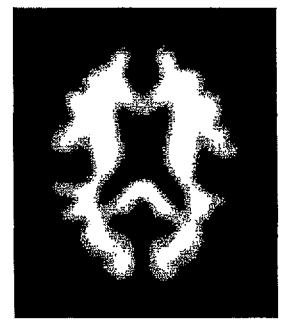
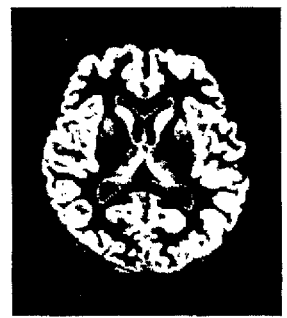
GREY MATTER IMAGE
SPATIAL NORMALIZATION
SMOOTHING

FIG.17

| TEST<br>DISEASE | POSITIVE | NEGATIVE |
|---|---|---|
| PRESENCE OF DISEASE | TP : TRUE POSITIVE | FN : FALSE NEGATIVE |
| ABSENCE OF DISEASE | FP : FALSE POSITIVE | TN : TRUE NEGATIVE |

MEDICAL IMAGE PROCESSING DEVICE

TECHNICAL FIELD

The present invention relates to a technique for processing a brain image obtained by MRI (Magnetic Resonance Imaging) etc., to assist in diagnosis of the brain disease, especially relates to a technique for processing a brain image obtained by MRI, etc. to suit for assisting in diagnosis.

BACKGROUND ART

Due to the aging society, patients with dementia have been increasing every year. There are various types in dementia, and it is necessary to distinguish the types at diagnosis to offer proper treatment.

In order to meet the demands above, recently, it becomes possible to obtain information regarding a state of the brain by nuclear medicine scanning such as SPECT (Single Photon Emission Computed Tomography) and PET (Positron Emission Tomography), or CT (Computerized Tomography) and MRI.

Consequently, it has been revealed that the phenomenon, such as blood flow and metabolism of a specific region of the brain decreases and atrophy of tissue thereof occurs, varies according to the types of disease, and thus a measurable assessment method for the above has been sought.

For example, decreasing of blood flow and metabolism in a certain portion of the brain can be examined by comparing SPECT or PET images.

Furthermore, regarding atrophy of tissue, it is possible to determine whether an abnormality is present by obtaining the volume of a specific region from an MRI image and comparing relative scales thereof.

As an assessment method of atrophy of tissue by use of such a brain image, VBM (Voxel Based Morphometry) is known. VBM is performed by processing a brain image obtained by imaging the head of a subject, with voxel (an image element in three dimensions) basis, (for example, see the patent document 1).

The VBM method is an effective assessment method for identifying the Alzheimer's disease, and it is reported that the diagnostic capability thereof for identifying an individual with the Alzheimer's disease from normal individuals is 87.8% (see the non-patent document 1).

PRIOR ART DOCUMENT

Patent Document

Patent document 1: Japanese Patent Application Laid-Open No. 2005-237441

Non-Patent Document

Non-patent document 1: Yoko Hirata, Hiroshi Matsuda, Kiyotaka Nemoto, Takashi Ohnishi, Kentaro Hirao, Fumio Yamashita, Takashi Asada, Satoshi Iwabuchi and Hirotsugu, Samejima, Voxel-based morphometry to discriminate early Alzheimer's disease from controls. Neurosci Lett 382:269-274, 2005
Non-patent document 2: Bookstein F L. "Voxel-based morphometry" should not be used with imperfectly registered images. Neuroimage. 2001; 14(6):1454-62.
Non-patent document 3: J. Ashburner and K. J. Friston. Unified segmentation. NeuroImage. 2005; 26: 839-851.
Non-patent document 4: Ashburner J, A fast diffeomorphic image registration algorithm. Neuroimage. 2007 Oct. 15; 38(1):95-113.
Non-patent document 5: Hiroshi Matsuda. Statistical Analysis of SPECT, Image Diagnosis of Alzheimer's Dementia, Medical View Co., Ltd., pp 76 to 86 (2001).

SUMMARY

Problems to be Solved by the Invention

However, there is a problem in brain image processing performed by the conventional method above that tissue separation processing is not successfully performed depending on target brain images, and accordingly it is difficult to specify tissue correctly.

The present invention was made in view of such problems, and an object of the present invention is to provide a medical image processing device that is capable of determining a state of an obtained brain image and adjusting the image to be suitable for being used in tissue separation processing.

Means for Solving the Problem

In order to achieve the object described above, a first aspect of the present invention provides a medical image processing device comprising: a target slice selection unit that selects a slice image to be processed as a target slice from a brain image that is configured by a plurality of slice images; a cerebral parenchyma measurement unit that performs measurement processing to determine an effective maximum value in the cerebral parenchyma of the brain image, which is an effective maximum value of signal values of image elements in the cerebral parenchyma; a brain image measurement unit that performs measurement processing to determine an effective maximum value of signal values of image elements in the whole brain image; a skull measurement unit that performs measurement processing to determine a peak average value around the skull, which is an average of signal values of image elements that are at peaks in a region around the skull of the brain image; a control processing determination unit that determines necessity of high-signal-value-control processing based on the effective maximum value in the cerebral parenchyma, the effective maximum value in the whole brain image, and the peak average value around the skull; and a high-signal-value-control processing unit that performs the high-signal-value-control processing with respect to the brain image when the control processing determination unit determines that the high-signal-value-control processing is necessary.

According to the first aspect of the present invention, a target slice of a brain image is selected and an effective maximum value of signal values of image elements in the cerebral parenchyma, an effective maximum value of signal values of image elements in a while brain image, and a peak average value as an average of signal values of image elements which are at peaks in a region around the skull are measured with respect to the selected slice so that high-signal-value-control processing is performed to the brain image when it is determined to be necessary based on the results of the measurement. Therefore, it is possible to determined a state of an objective brain image and adjust the brain image to be suitable for tissue separation processing.

A second aspect of the present invention provides the medical image processing device according to the first aspect of the present invention, wherein the control processing determination unit performs a skull region determination to determine whether the peak average value around the skull is higher at a constant rate than the effective maximum value in the cerebral parenchyma, and also performs a whole image determination to determine whether the signal values in the whole image are higher at a constant rate than the effective maximum value in the cerebral parenchyma, and when either the skull region determination or the whole image determination satisfies the condition, it is determined that the high-signal-value-control processing is necessary.

According to the second aspect of the present invention, determination whether a peak average value in a region around the skull and signal values in a whole image are higher at a constant rate than an effective maximum value in the cerebral parenchyma is performed, and when one of the peak average value in the region around the skull and the signal values in the whole image are higher at a constant rate than the effective maximum value in the cerebral parenchyma, it is determined that high-signal-value-control processing is necessary. Therefore, it is possible to accurately determine necessity of the high-signal-value-control processing in both cases where signal values in the region around the skull are significantly higher than those in the cerebral parenchyma, and cases where signal values in a portion other than the region around the skull and the cerebral parenchyma are significantly higher than those in the cerebral parenchyma.

A third aspect of the present invention provides the medical image processing device according to the first aspect or the second aspect of the present invention, wherein, with respect to each slice image, the target slice selection unit sets a predetermined line segment within an image, obtains a length between image elements of which distance therebetween is the largest among image elements that are on the line segment with signal values higher than a predetermined value, and selects a target slice, in which said length between image elements is longer than the length determined by a predetermined ratio based on the maximum said length among all the slice images.

According to the third aspect of the present invention, a target slice will be selected from such sliced images that said length between image elements with their signal value is higher than predetermined level is longer than the length determined by a predetermined ratio based on the maximum said length among all the slice images. Therefore, the suitable slice image not including high signal values in the region other than the skull or the cerebral parenchyma can be selected for the use of determining necessity of the high-signal-value-control processing.

A fourth aspect of the present invention provides the medical image processing device according to any one of the first aspect to the third aspect of the present invention, wherein, with respect to the selected each target slice, the cerebral parenchyma measurement unit sets a predetermined number of line segments that cross over a center part of a brain, divides, for the every line segment, the signal value distribution of image elements on one of the line segment into a predetermined number of regions so as to set a predetermined number of regions at a center of the signal value distribution as a cerebral parenchyma region, acquires a histogram of signal values in the cerebral parenchyma region, and obtains a maximum of signal values that are left after excluding upper predetermined image elements as an effective value in the cerebral parenchyma.

According to the fourth aspect of the present invention, with respect to the selected each target slice, the cerebral parenchyma measurement unit sets predetermined number of line segments that cross over a center part of a brain, divides, for every line segment, the signal value distribution of image elements on one of the line segment into a predetermined number of regions, acquires a histogram of signal values in the cerebral parenchyma region, the cerebral parenchyma region corresponding central part of each line segment, consisting of certain number of the regions, then calculates the maximum of all the signal values left after excluded upper predetermined image elements to determine an effective value of the cerebral parenchyma.

Therefore, it is possible to accurately obtain the effective maximum value of the cerebral parenchyma that represents the cerebral parenchyma.

A fifth aspect of the present invention provides the medical image processing device according to any one of the first aspect to the fourth aspect of the present invention, wherein the brain image measurement unit acquires a histogram of signal values of image elements in a whole target slice, then calculates the maximum of all the signal values that are left after excluded upper predetermined image elements to determine an effective maximum value in a whole image.

According to the fifth aspect of the present invention, a histogram of signal values of image elements in a whole target slice is acquired to obtain the maximum value of all the signal values that are left after excluding upper predetermined image elements as an effective maximum value in the whole image. Therefore, it is possible to accurately obtain the effective maximum value in the whole image which is a value representing the whole image.

A sixth aspect of the present invention provides the medical image processing device according to any one of the first aspect to fifth aspect of the present invention, wherein, with respect to the selected each target slice, the skull measurement unit sets a predetermined number of line segments that cross over a center part of a brain, divides, for every line segment, the signal value distribution of image elements on one of the line segment into a predetermined number of regions, acquires a maximum value of signal values in the skull region, the skull region corresponding either end of each line segment, consisting of certain number of the regions, then calculates an average of the maximum value among all the line segments on all the target slices to determine an peak average value of the skull.

According to the sixth aspect of the present invention, with respect to each target slice, signal value distributions that are created respectively for a plurality of line segments that cross over a center part of the brain are divided into a predetermined number of regions such that a predetermined number of regions at both ends are set as a region around the skull, and an average value of maximum signal values in the region around the skull for the every line segment of all the target slices is obtained as a peak average value around the skull. Therefore, it is possible to accurately obtain the peak average value around the skull which is a value representing the region around the skull.

A seventh aspect of the present invention provides the medical image processing device according to any one of the first aspect to sixth aspect of the present invention, wherein the high-signal-value-control processing unit realizes the high-signal-value-control processing relatively by controlling in such a way that a signal value of an image element is unchanged if its signal value is lower than a predetermined value, a signal value of an image element is limited to the predetermined value if its signal value is equal to or higher than the predetermined value According to the seventh aspect of the present invention, a signal value in an image element, which is smaller than a predetermined value is kept unchanged but a signal value of an image element, which is greater than the predetermined value is processed so as to become the predetermined value. Therefore, it is possible to control a high signal value of the input image.

A eighth aspect of the present invention provides the medical image processing device according to any one of the first aspect to sixth aspect of the present invention, wherein the high-signal-value-control processing unit realizes the high-signal-value-control processing relatively by controlling in such a way that a signal value of an image element is unchanged if its signal value is lower than a predetermined value, a signal value of an image element is lowered than the original thereof if its signal value is equal to or higher than the predetermined value.

According to the eighth aspect of the present invention, a signal value of an image element, which is smaller than a predetermined value is kept unchanged but a signal value of an image element, which is greater than the predetermined value is processed so as to become smaller than an original value thereof. Therefore, it is possible to control a high signal value of the input image.

A ninth aspect of the present invention provides the medical image processing device according to the eighth aspect of the present invention, wherein the high-signal-value-control processing unit realizes the high-signal-value-control processing relatively by controlling in such a way that a signal value of an image element is unchanged if its signal value is lower than a predetermined value, a signal value of an image element is transformed by a linear function of which gradient equals to zero or is positive and smaller than 1.

According to the ninth aspect of the present invention, a signal value of an image element, which is smaller than a predetermined value is kept unchanged but a signal value of an image element, which is greater than the predetermined value is transformed by a linear function of which a gradient is greater than or equals to 0 and is smaller than 1. Therefore, it is possible to control a high signal value of the input image, and an image as a result of tissue separation processing becomes more natural.

Effect of the Invention

According to the present invention, it becomes possible to determine a state of an obtained brain image and adjust the image to be suitable for being used in tissue separation processing.

BRIEF DESCRIPTION OF DRAWINGS

FIG. 7 illustrates signal value distributions of the cerebral parenchyma and a region around the skull.

FIG. 8 illustrates measurement processing of an effective maximum value in the cerebral parenchyma and a peak average value around the skull.

FIG. 13 is a conceptual diagram illustrating a result of spatial normalization and smoothing.

FIG. 17 is a chart illustrating the relationship between a negative or positive test result and the presence of the disease.

BEST MODE FOR CARRYING OUT THE INVENTION

Figure 1:
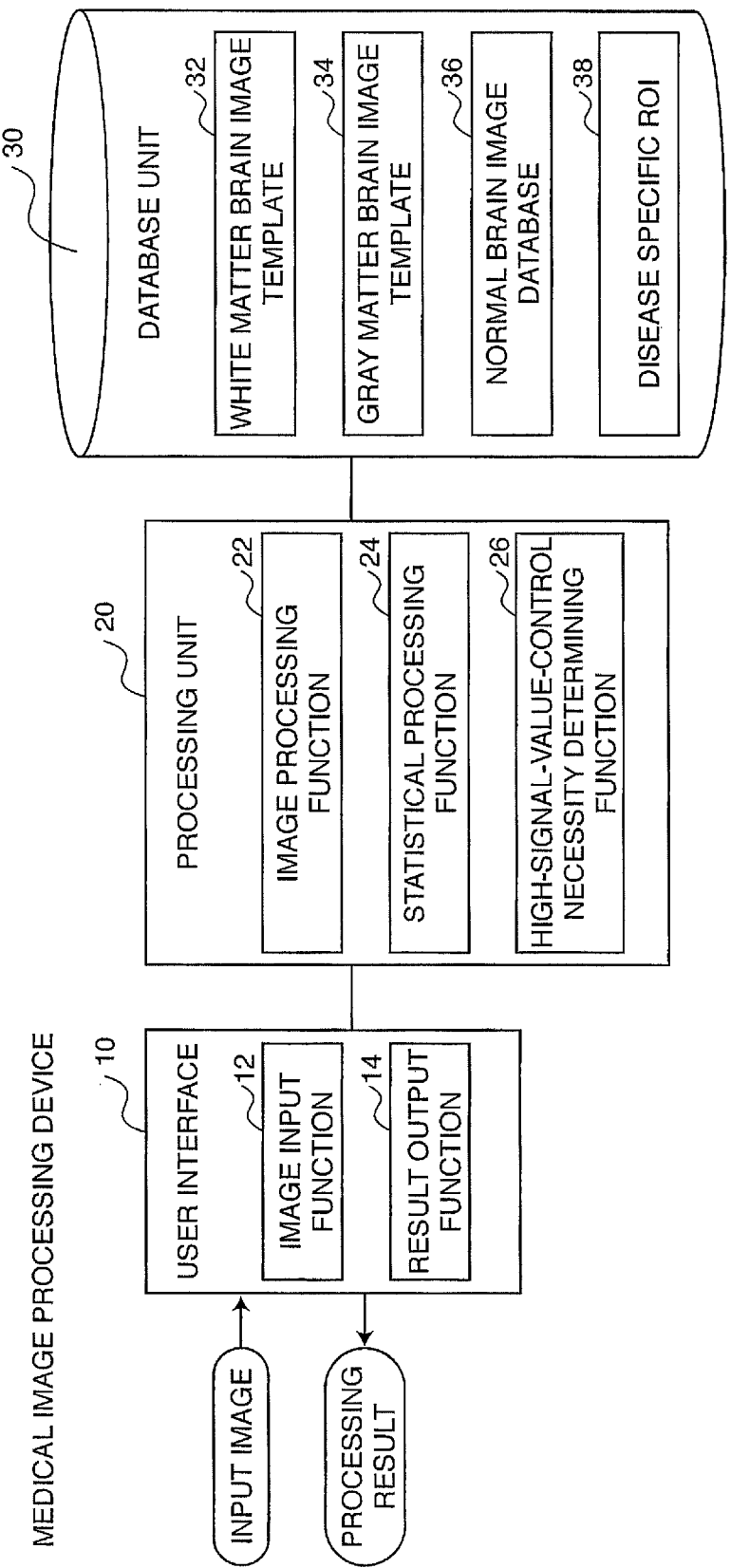
FIG. 1 is a block diagram illustrating an outline of a medical image processing device according to an embodiment of the present invention.

Hereinafter, a preferred embodiment according to the present invention will be described with reference to the drawings. FIG. 1 is a block diagram of a medical image processing device according to an embodiment of the present invention. The medical image processing device according to the present embodiment, which is illustrated in FIG. 1, includes a user interface 10, an image and statistical processing unit 20, and a database unit 30.

The user interface 10 includes an image input function 12 that inputs an MRI image as an input image and a result display function 14 that displays a processing result after being processed by the image and statistical processing unit 20. The image and statistical processing unit 20 includes an image processing function 22 that processes the MRI image input from the user interface 10, a statistical processing function 24 that calculates various statistics, etc., and a high-signal-value-control necessity determining function 26 that determines necessity of high-signal-value control with respect to the input image. Furthermore, the database unit 30 stores therein a white matter brain image template 32, a gray-matter brain image template 34, a normal brain image database 36, disease specific ROI 38, etc., which are used in processing performed by the image and statistical processing unit 20 as described later.

Figure 2:
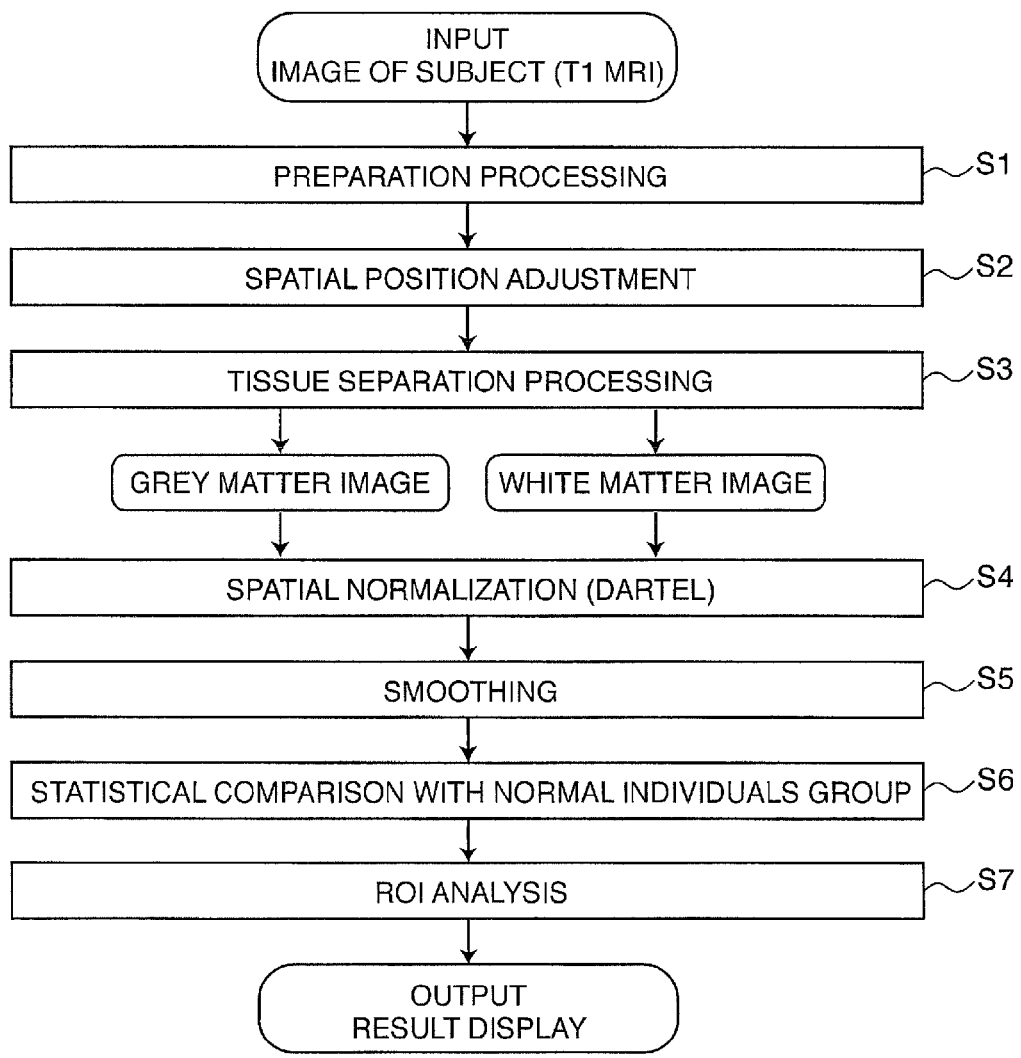
FIG. 2 is a flowchart illustrating basic processing procedures of a medical image processing method according to the present embodiment.
Figure 3:
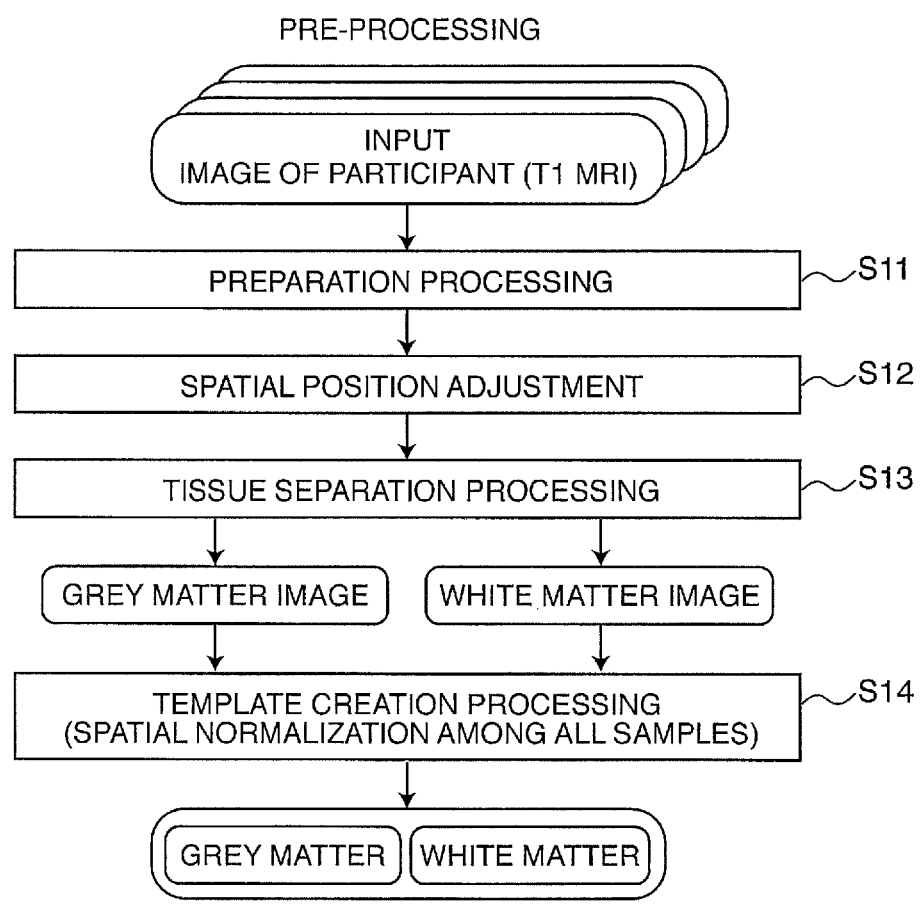
FIG. 3 is a flowchart illustrating pre-processing procedures of a medical image processing method according to the present embodiment.

FIG. 2 is a flowchart illustrating an outline of processing of a medical image processing device according to the present embodiment. FIG. 3 is a flowchart illustrating pre-processing procedures of a medical image processing method according to the present embodiment. In FIG. 2, firstly, when an MRI brain image of a subject is input, a predetermined processing is performed with respect to the brain image, whether high-signal-value-control processing should be performed is determined, and the high-signal-value-control processing is performed according to the result of determination (Step S1). At the Step S1, there is a case where the high-signal-value-control processing is not performed according to the result of determination. The processing at the Step S1 is the essential feature of the present invention. Details of Step S1 will be described later.

Next, position adjustment with respect to the brain image to which high-signal-value-control is processed (in the case where the high-signal-value-control processing is not performed, the input MRI brain image) is performed to correct a spatial gap (Step S2). Thereafter, a gray matter image presenting the gray matter and a white matter image presenting the white matter gray are created from the position-adjusted brain image by tissue separation processing (Step S3).

Next, spatial normalization using the DARTEL (Diffeomorphic Anatomical Registration Through Exponentiated Lie Algebra) algorithm as described later is performed with respect to the created both images (Step S4), and then smoothing is performed with respect to the normalized white matter image and the gray matter image respectively (Step S5).

Thereafter, statistical comparison is performed between the smoothed both images and white matter and gray matter images of normal individuals respectively (Step S6), and ROI analysis is performed (Step S7) to output an analysis result as a diagnostic outcome and provide it to assist diagnosis.

In the present embodiment, the Steps S1 to S7 described above can be processed by a program of the image and statistical processing unit 20 that is configured by a computer. Similarly, a procedure of creating templates of white matter and gray matter through the respective Steps S11 to S14, which will be described below, can be processed by a program.

Before performing the basic processing flow of the Steps S1 to S7, pre-processing of creating templates that are used in the spatial normalization at the Step S4 is performed at the Steps S11 to S14 illustrated in FIG. 3.

Firstly, T1-weighted MRI brain images (images of participants in FIG. 3) that are obtained from as many normal individuals as possible are input.

Figure 4:
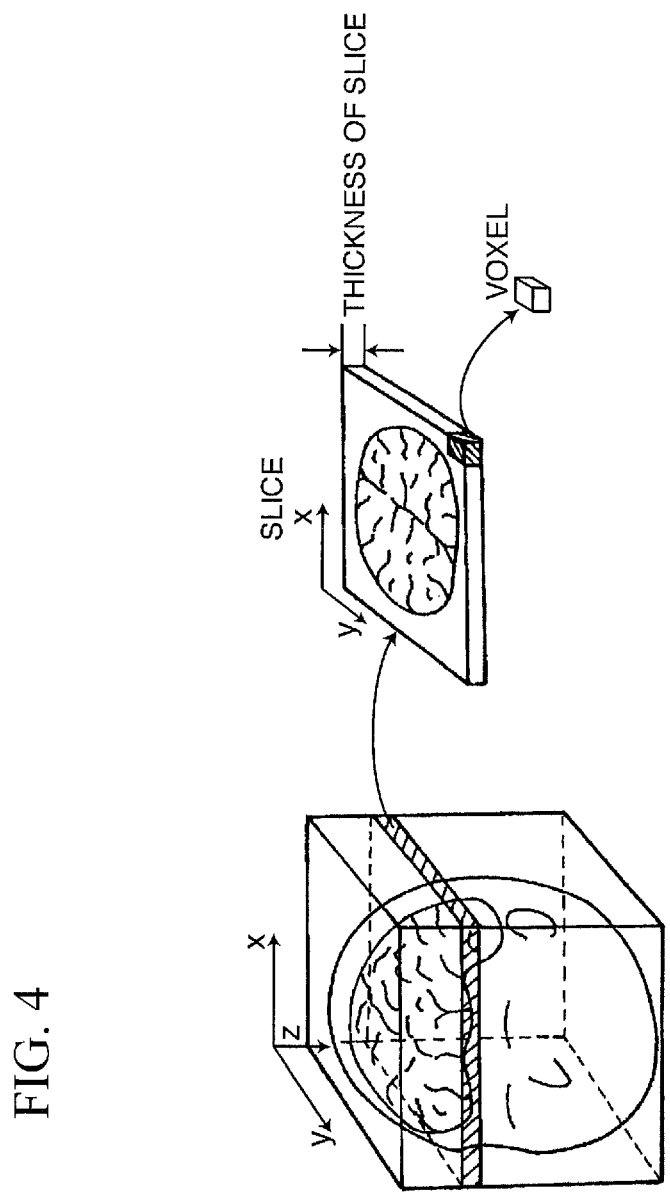
FIG. 4 is a conceptual pattern diagram illustrating the features of a slice image and a vexel.

Pretreatment processing is conducted for the MRI brain images obtained from respective participants. Specifically, as indicated in FIG. 4 illustrating a conceptual view of the whole brain and a slice image of a part of the brain, for example, the 100 to 200 pieces of T1-weighed MRI brain images, in which the whole brains are imaged in slice with a predetermined thickness so as to include the whole brains of participants, are input. Furthermore, re-sampling of the slice images is performed such that the length of respective sides of a voxel of each slice image equals therebetween beforehand. A voxel herein represents a unit of a coordinate of an image having the "thickness" and corresponds to a pixel of a two dimensional image.

After inputting the MRI brain images that have been pretreated above, whether an imaging direction and resolution of the each slice image satisfies a system-preset condition is checked.

When it is confirmed that MRI brain images input are satisfying the preset condition, preparation processing is performed (Step S11). In the preparation processing, whether the high-signal-value-control processing with respect to the input image should be performed is determined so that the tissue separation processing is correctly performed in the process of creating templates, and when it is determined to be necessary, the high-signal-value-control processing is performed.

Figure 5:
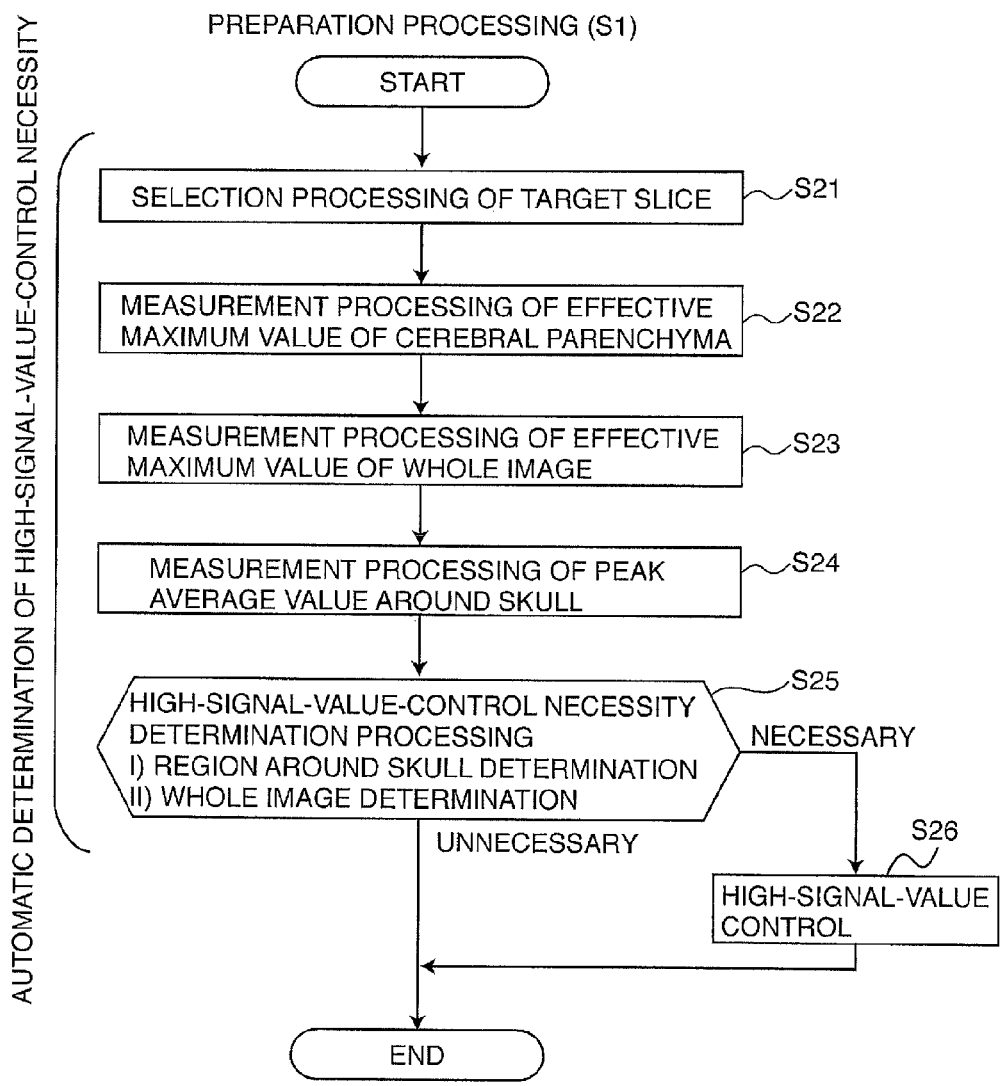
FIG. 5 is a flowchart illustrating details of preparation processing.
Figure 6:
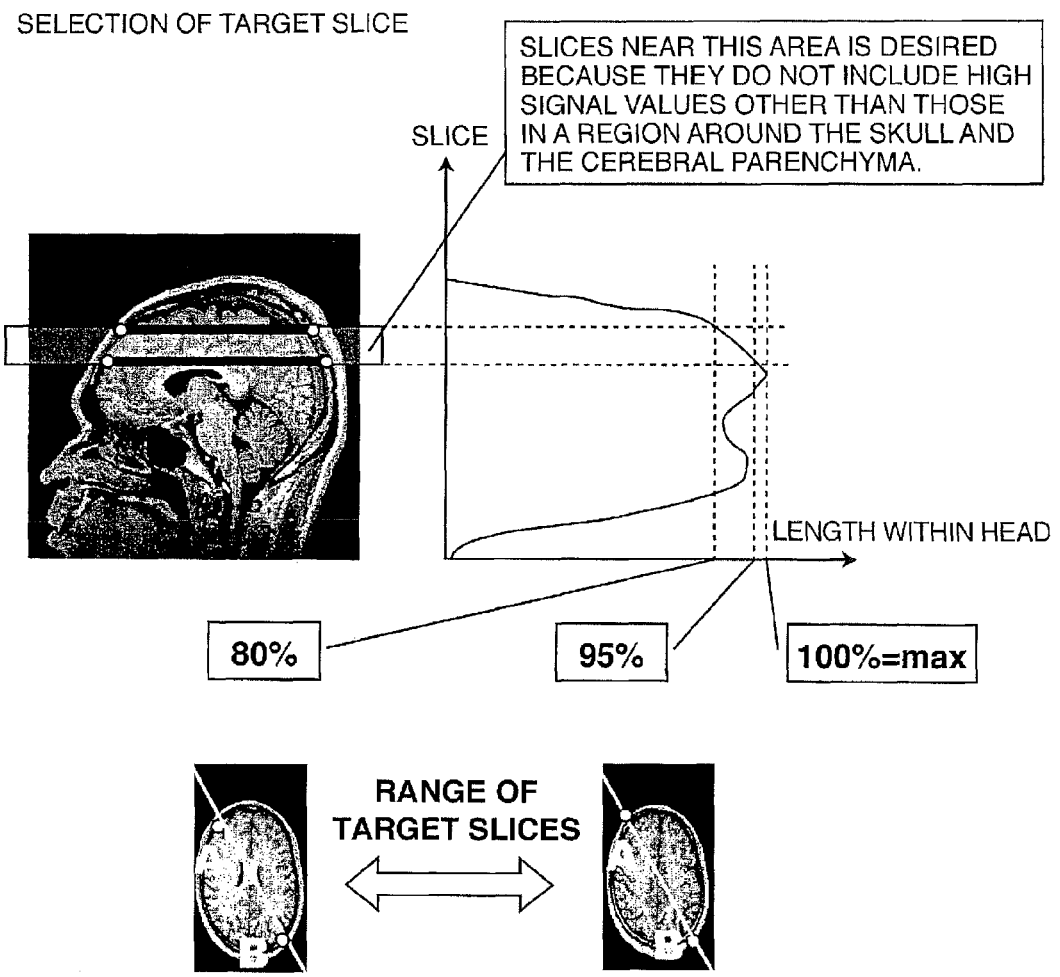
FIG. 6 illustrates selection processing of a target slice.

FIG. 5 is a flowchart of details of the preparation processing. Firstly, a selection processing is performed to select a target slice from the input images to be used (Step S21). FIG. 6 illustrates the selection processing of a target slice. As a target slice, it is desired to select a portion in which a high signal value is not included, other than a region around the skull and the cerebral parenchyma. It is desirable to select a portion not including high signal value anywhere other than regions around the skull and the cerebral parenchyma.

Specifically, with respect to each slice image, a predetermined line segment is set within a slice image, and the length between image elements of which the distance therebetween is the largest is obtained from image elements located on the line segment and presenting signal values higher than a predetermined value. As a line segment to be set within an image, the one which crosses over a large portion of the imaged region around the skull and the cerebral parenchyma is set. Since the captured image is, usually, in the form of a square, in which the skull and the cerebral parenchyma are centrally located, a diagonal line of the image will be used as the line segment described above. the above-described predetermined value used for comparing to a signal value can be set appropriately, for example, a value obtained by multiplying an average of signal values in the whole image by a predetermined constant may be used.

An image element of which the signal value is higher than the predetermined value represents the region around the skull, and the length between image elements of which distance therebetween is the largest among image elements presenting higher signal values than a predetermined value represents the length of a portion where the line segment overlaps the head. As described above, as a target slice, it is desired to select a slice not including high signal value anywhere other than regions around the skull and the cerebral parenchyma, and the portion is located at a position where the length becomes 80 to 95% of the largest portion of the head. In the present embodiment, therefore, a slice image having the largest length between image elements are specified, and the one in which the length between image elements to be 80 to 95% of that of the specified slice images is selected as a target slice.

After selecting a target slice, processing for measuring an effective maximum value in the cerebral parenchyma is performed (Step S22). Before measuring an effective maximum value in the cerebral parenchyma, firstly, a signal value distribution of the cerebral parenchyma is obtained. When obtaining the signal value distribution of the cerebral parenchyma, a signal value distribution of the region around the skull is obtained as well. FIG. 7 illustrates the signal value distribution of the cerebral parenchyma and that of the region around the skull. In order to obtain a signal value distribution, firstly, a predetermined number of line segments that cross over the center of the brain are respectively set in the selected target slices. As illustrated in FIG. 7 (b), ten line segments are set in the present embodiment. Then, signal values of the image elements thereon are plotted for each line segment. Thereafter, the signal value distribution is divided into a predetermined number of regions in accordance with the line segments so that a predetermined number of central regions are assumed as cerebral parenchyma region and a predetermined number of regions of both ends are assumed as regions around the skull. In the present embodiment, as illustrated in the signal value distribution on the right side of FIG. 7 (a), the signal value distribution is divided into ten regions such that the four regions at the central part of the distribution is assumed the cerebral parenchyma region and each one region of the both ends of the distribution (a total of two) is assumed to be the region around the skull. Reference signs A and B in the signal value distribution correspond to those of A and B in the brain image illustrated at the left side of FIG. 7 (a).

Next, a histogram of signal values in the cerebral parenchyma regions of all the target slices is obtained, and a maximum value in the case of excluding a portion which is considered to be affected by high signal artifact (noise by an MRI) is obtained as an effective maximum value in the cerebral parenchyma "Bmax". Although which portion should be excluded may be set appropriately as considered to be affected by high signal artifact, specifically, the top thHa % of the image elements of the histogram are excluded. In the present embodiment, it is set that thHa=3. FIG. 8 (*a*) illustrates the measurement processing of an effective maximum value in the cerebral parenchyma. As illustrated in a histogram on the lower part of FIG. 8 (*a*), the value of a portion indicated with an arrow which excludes the shaded top 3% is determined to be the effective maximum value in the cerebral parenchyma "Bmax".

Next, processing for measuring an effective maximum value in the whole image is performed (Step S23). Specifically, a histogram of signal values of image elements in the square-shaped whole target slice is obtained, and a maximum value in the case of excluding a portion affected by high signal artifact is obtained as an effective maximum value in the whole image "Imax". Although which portion should be excluded may be set appropriately as considered to be affected by the high signal artifact, specifically, the top thHb % of the image elements of the histogram are excluded. In the present embodiment, it is set that thHb=1.

Next, processing for measuring a peak average value around the skull is performed (Step S24). Specifically, a maximum signal value is extracted from the region around the skull that is set at the Step S22. The maximum signal value in the region around the skull is found in the circled two portions in the signal value distribution on the right side of FIG. 7 (*a*). The extraction processing above is performed for every line segment of all the target slices to calculate an average value of the extracted signal values. FIG. 8 (*b*) illustrates the measurement processing of a peak average value around the skull. In the present embodiment, as illustrated in FIGS. 7 (*a*) and 7 (*b*), two signal values are extracted from one line segment, and thus the 20 signal values are extracted from one piece of target slice. Therefore, an average of the product obtained by multiplying the number of pieces of the target slices by 20 signal values is calculated as a peak average value "Pave" of the region around the skull.

Next, processing for determining necessity of high signal value control is performed (Step S25). Specifically, two options of determination, that is, a skull region determination and a whole image determination are performed. When one of the two options satisfies determination conditions, it is determined that the high signal value control is necessary, and when none of the two options satisfies the determination conditions, it is determined that the high signal value control is unnecessary.

The skull region determination is performed to determine whether signal values in the region around the skull are higher at a constant rate than those in the cerebral parenchyma region. Specifically, processing according to the "Equation 1" described below is performed.

$$th1*(\text{the effective maximum value in the cerebral parenchyma "Bmax"}) < (\text{the peak average value "Pave"}) \quad \text{[Equation 1]}$$

In the [Equation 1] described above, th1 is a coefficient that defines the degree to which the signal values in the region around the skull can be permissive as compared with those in the cerebral parenchyma region. While th1 can be appropriately set, in the present embodiment, it is set that th1=1.8. It is determined whether the condition that is shown in the [Equation 1] described above is satisfied, and when it is satisfied, it is determined that high-signal-value control is necessary. This is because, when the peak average value in the region around the skull is higher at a constant rate than the effective maximum value in the cerebral parenchyma, it reveals necessity to be controlled for the high signal values in the region around the skull.

On the other hand, the whole image determination is performed to determine whether signal values in the whole image are higher at a constant rate than those in the cerebral parenchyma region. Specifically, processing according to the "Equation 2" described below is performed.

$$th2*(\text{the effective maximum value in the cerebral parenchyma "Bmax"}) < (\text{the effective maximum value in the whole image "Imax"}) \quad \text{[Equation 2]}$$

In the [Equation 2] described above, th2 is a coefficient that defines the degree to which the signal values in the whole image, which includes any portion other than the cerebral parenchyma, can be permissive as compared with those in the cerebral parenchyma region. While th2 can be appropriately set, in the present embodiment, it is set that th2=1.7. It is determined whether the condition that is shown in the [Equation 2] described above is satisfied, and when it is satisfied, it is determined that high-signal-value control is necessary. This is because, when the effective maximum value in the whole image is higher at a constant rate than the effective maximum value in the cerebral parenchyma, it reveals necessity to be control for the high signal values other than those in the cerebral parenchyma.

When one of the skull region determination and the whole image determination satisfies the condition, that is, either of the equations of the [Equation 1] or the [Equation 2] is satisfied, the flow advances to the step of high-signal-value-control processing (Step S26). Adversely, when none of the skull region determination and the whole image determination satisfies the condition, that is, neither the [Equation 1] nor the [Equation 2] is satisfied, high-signal-value-control processing is not performed and consequently, the preparation processing is finished. This is because, the fact, in which none of the skull region determination nor the whole image determination satisfies the condition, indicates that the high value signals other than those in the cerebral parenchyma are not too high to prevent the tissue separation processing, and thus the high-signal-value-control processing is not required. At the Step S25, it does not matter which of the determination, that is, the skull region determination and the whole image determination is performed first, and when the one which is performed first satisfies the condition, the flow advances to the high-signal-value-control processing (Step S26) without determining whether the other one satisfies the condition.

The high-signal-value-control processing (Step S26) is described below. The high-signal-value-control processing is performed to control a value of an image element having a high signal value among image elements of the input image in order to prevent the value from being relatively any higher. Accordingly, as long as the processing is configured to control a value of an image element having a high signal value among image elements of the input image not to be relatively any higher, various methods can be employed. In the present embodiment, as a first method, a high-signal-value-control processing is realized such that an image element with signal value higher than a certain constant value to be limited its signal value to the constant and an image element with signal value less than the constant to be kept its signal value unchanged.

In the present embodiment, processing according to the "Equation 3" described below is performed so that the signal value s (x, y) of each image element (x, y) of the input image is corrected to the signal value s' (x, y).

$$s'(x,y) = th3 \quad \text{[Equation 3]}$$

Only where s (x, y)≥th3.

In the [Equation 3] described above, th3 is a threshold of the signal value of the image element that is to be controlled. In the present embodiment, it is set that th3=(the effective maximum value in the cerebral parenchyma "Bmax").

Furthermore, in the present embodiment, as a second method, another high-signal-value-control processing is realized such that an image element with signal value higher than a certain constant value to be converted its signal value by a linear function of which gradient "α" is greater than 0 and smaller than 1 and an image element with signal value less than the constant to be kept its signal value unchanged. Thereby, signal value of an image element with signal value higher than a constant changes moderately than that of an image element with signal value less than the constant, and accordingly it is possible to control the value of the image element having a high signal value not to be relatively high. With the second method, the signal value higher than a constant value increases gradually, and thus resultant image of tissue separation processing becomes more natural.

In the present embodiment, as the second method, processing according to the "Equation 4" described below is performed so that the signal value s (x, y) of respective image elements (x, y) of the input image is corrected to the signal value s' (x, y).

$$s'(x,y)=th3+a(s(x,y)-th3)$$ [Equation 4]

Only where s (x, y)≥th3.

In the [Equation 4] described above, th3 is a threshold of the signal value of the image element that is to be controlled. In the present embodiment, it is set that th3=(the effective maximum value in the cerebral parenchyma "Bmax"). In addition, in the present embodiment, it is set that "a" is a coefficient, which equals 0.2.

While the high-signal-value control is realized by processing according to the [Equation 3] or the [Equation 4] described above in the present embodiment, the high-signal-value control can be realized by other known methods such as gamma correction as long as a signal value of an image element having a signal value higher than a certain constant is converted to smaller than the original.

After the preparation processing is completed, the procedure returns the flowchart in FIG. 3 to perform further processing. In the Steps S12 to S14, regarding an image in which signal values are controlled, the corrected image becomes a target of processing, and regarding an image with signal values uncontrolled, an input image remains as a target of processing.

Firstly, spatial-position-adjustment processing is performed (Step S12). The spatial-position-adjustment processing corresponds to correcting a spatial position and angle by a linear transformation (an affine transformation) in order to increase accuracy at the time of comparing a brain image to be examined to a normal brain image.

After the spatial-position-adjustment processing is completed, tissue separation processing is performed (Step S13) to create a white matter image showing white matter that is extracted as well as a gray matter image showing gray matter that is extracted, respectively.

In the T1-weighed MRI brain image that has been input, there are three kinds of tissue, that is, white matter that corresponds nerve fibers and presents a high signal value, gray matter that corresponds nerve cells and presents an intermediate signal value, and cerebrospinal fluid that presents a low signal value, and accordingly processing for extracting white matter and gray matter respectively is performed by focusing on the difference therebetween. The tissue separation processing is explained in the patent document 1 mentioned above. In the present invention, integrative tissue separation processing that provides better accuracy in extraction than that of the processing in the patent document 1 is performed. The integrative tissue separation processing is a method for tissue separation, in which normalization, tissue separation, and correction of ununiform signals are incorporated in one model. The details thereof are explained in the non-patent document 3 mentioned above. The integrative tissue separation processing has the features that not only creates a white matter image and a gray matter image but also creates a field for transformation which indicates a correspondent relationship of the coordinates of an MRI image and that of a normal brain image. gray The field for transformation is used in normalization that will be described later.

In this way, white matter images and gray matter images presenting white matter and gray matter that are three-dimensionally extracted respectively from a number of MRI images of normal individuals by performing tissue separation, are obtained beforehand as a number of samples.

As described above, white matter images presenting white matter that is extracted from a number of (a plurality of) respective MRI images of normal individuals by performing tissue separation, are created as samples, and then a white matter template is created by spatial normalization performed among all the created samples (Step S14). Similarly, gray matter images presenting gray matter that is extracted from a number of (a plurality of) respective MRI images of normal individuals by performing tissue separation, are created as samples, and then a gray matter template is created by spatial normalization performed among all the created samples.

To the spatial normalization performed herein, the DARTEL (Diffeomorphic Anatomical Registration Through Exponentiated Lie Algebra) algorithm is applied.

In order to overcome the low accuracy according to the conventional VBM method, John Ashburner developed DARTEL (Diffeomorphic Anatomical Registration Through Exponentiated Lie Algebra) that is a new type of the VBM method (see the non-patent document 4).

DARTEL has more accuracy in spatial normalization than that of the conventional VBM method, and therefore it is expected to contribute to improving the diagnostic capability by statistical image analysis of the Alzheimer's disease. Furthermore, spatial normalization according to DARTEL is performed more precisely than the conventional method so that not only gray matter that has been a target of assessment so far, but also white matter can be a target of assessment.

In template creation processing at the Step S14, respective stratified templates of white matter and gray matter are created in accordance with attributes of the participants such as participants' age and sex, and the created temples are stored in the database unit 30 as the white matter brain image template 32 and the gray-matter brain image template 34.

Figure 9:
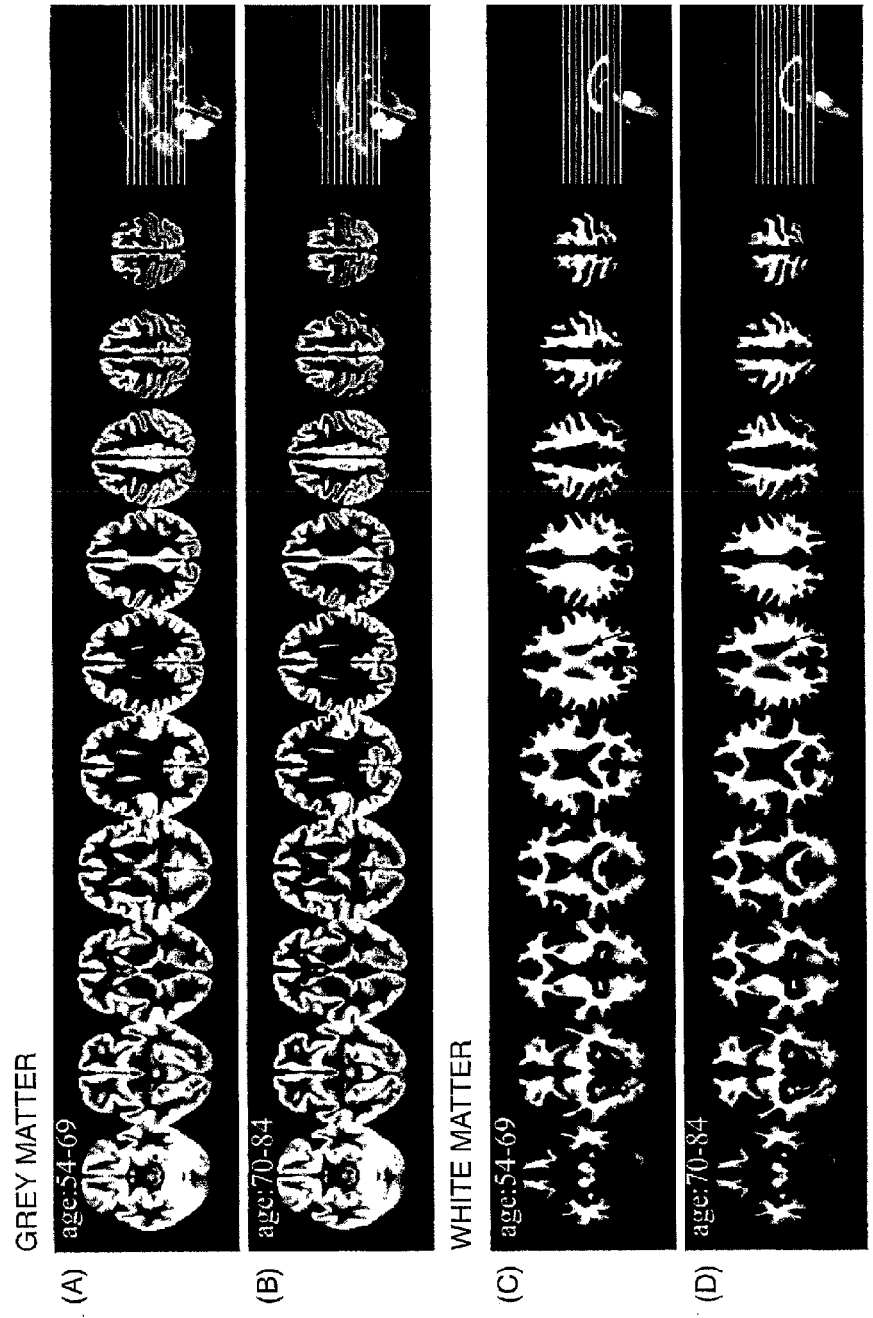
FIG. 9 is a conceptual diagram illustrating templates of gray matter and white matter by age.

The white matter templates and the gray matter templates are created by age of the participants as illustrated in FIG. 9. The gray matter (A) and the white matter (C) are created based on images of each normal individual at the age of 54 to 69, and the gray matter (B) and the white matter (D) are created based on images of each normal individual at the age of 70 to 84. As illustrated in FIG. 9, the templates are different between each age, and especially in the case of white matter, it is obvious that ventricular size indicated with arrows in sixth templates from the left is greatly different between the white matter (C) and the white matter (D).

Figure 10:
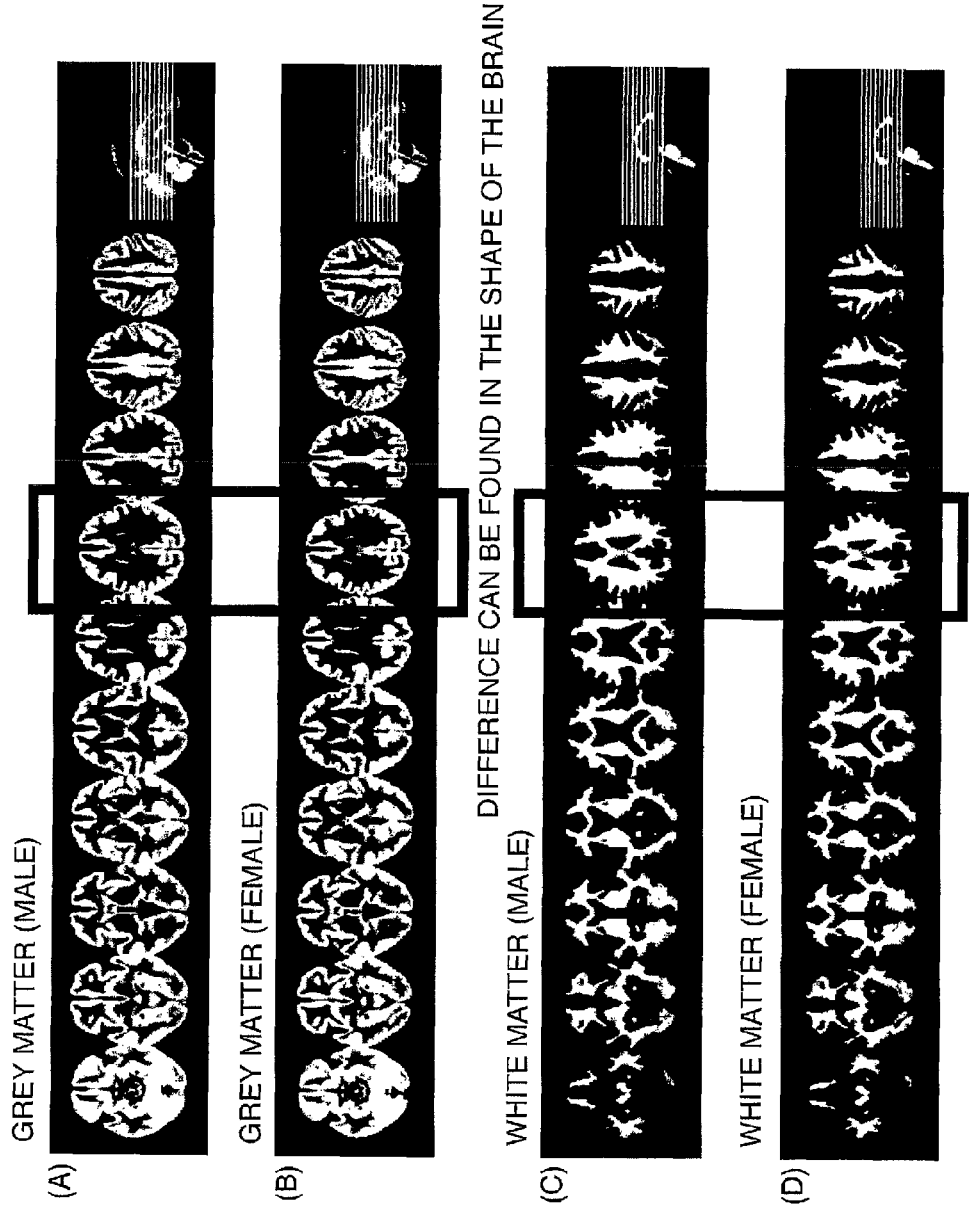
FIG. 10 is a conceptual diagram illustrating templates of gray matter and white matter by sex.

Furthermore, the white matter templates and the gray matter templates are created by sex of the participants as illustrated in FIG. 10. When comparing the templates at the positions enclosed in boxes in FIG. 10 for male and female, there can be found a difference in the shape of the brain ventricle between the sexes.

On the premise that the white matter and gray matter templates created as above are prepared by age and sex of the participants, diagnostic-assistance-information creation processing according to the Steps S1 to D7 is performed. Hereinafter, the white matter and gray matter templates described above are called the DARTEL templates.

Firstly, T1-weighed MRI image in which the brain is imaged in slice with a predetermined thickness is input as an image of a subject, and re-sampling of the slice images is performed such that the length of respective sides of a voxel of each slice image equals therebetween beforehand.

Next, the high-signal-value-control processing at the Step S1 is performed in the same manner as the case of the pre-processing at the Step S11.

Next, the spatial-position-adjustment processing at the Step S2 is performed in the same manner as the case of the pre-processing at the Step S12.

After the spatial-position-adjustment is completed, the tissue separation at the Step S3 is performed.

The tissue separation above is performed in the same manner as the case of the Step S13 to create a white matter image and a gray matter image of the subject showing white matter and gray matter that is extracted.

With respect to the white matter image and the gray matter image of the subject created as above, the spatial normalization processing at the Step S4 is performed. In the spatial normalization processing performed herein, the DARTEL algorithm is used in the same manner as the case at the Step S14.

The spatial normalization processing is performed to comprehensively correct the size of the whole brain and to locally correct the partial size of the brain so that anatomic differences among individual brain images is absorbed. Hereinafter, the case of gray matter will be mainly described for reason of expediency, however, substantially the same processing is performed in the case of white matter.

The spatial normalization processing using the DARTEL algorithm at the Step S4 is configured by the following three steps.

(Step S4-1) Initial position determination processing
(Step S4-2) Transformation processing to a DARTEL template
(Step S4-3) Transformation processing to a normal brain template In the initial position determination processing at the Step S4-1, processing for determining an initial position with respect to a gray matter image and a white matter image is performed by using the field for transformation to a normal brain, which has been obtained by the integrative tissue separation processing described above. In the initial position determination processing, the rigid body transformation is performed, and accordingly the shape of an image remains unchanged.

In the transformation processing to a DARTEL template at the Step S4-2, the DARTEL algorithm is used to the image that has been processed at the Step S4-1 to fit the shape thereof to a DARTEL template.

In the transformation processing to a normal brain template at the Step S4-3, the image being fit to the DARTEL template, which is obtained in the Step S4-2, is processed to be fit to a normal brain template. A field for transformation where the DARTEL template is transformed to the normal brain template is obtained beforehand, and transformation to a normal brain coordinate system is performed by utilizing the field for transformation.

In the processing at the Steps S4-1 and S4-2, normalization is performed while the sum of signal values of each voxel is maintained, and accordingly information about the volume is maintained and thus it becomes possible to measure the volume after the normalization is completed.

Figure 11:
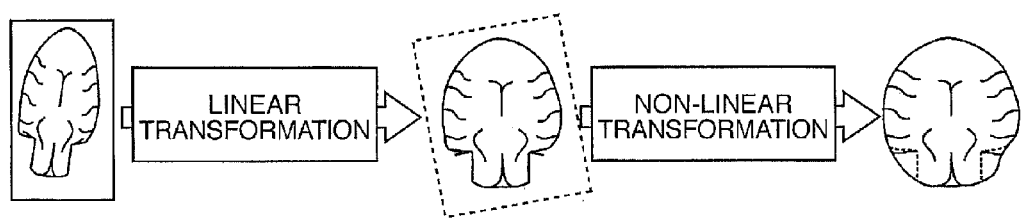
FIG. 11 is a conceptual pattern diagram illustrating the feature of spatial normalization processing.

A linear transformation is performed at the Step S4-1 and a linear transformation and a non-linear transformation are performed at the Steps S4-2 and S4-3. The Step S3-2 is described below as an example. As the features of the processing is conceptually-illustrated in FIG. 11, image processing is performed using a linear transformation and a non-linear transformation so as to minimize the sum of squares of errors between the image of the subject and the average gray-matter brain image template 34 that is created at the Step S14 and read from the database unit 30. In the spatial normalization processing, comprehensive correction of the position, size, and angle is performed by a linear transformation initially, and then local correction of the shape such as unevenness is performed by a non-linear transformation.

Figure 12:
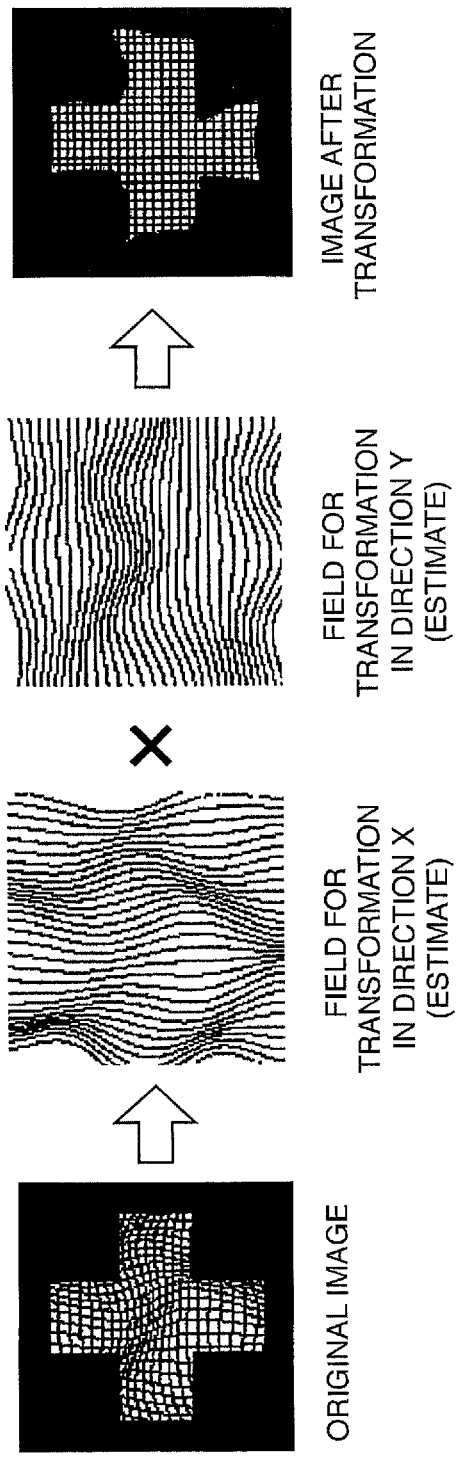
FIG. 12 is a conceptual diagram illustrating the features of non-linear transformation.

The linear transformation performed herein is an affine transformation performed in the same manner as the case of the position adjustment at the Step S2. Furthermore, as a conceptual view of the processing is illustrated in FIG. 12, the non-linear transformation is performed to estimate a field for transformation that represents a local displacement in each direction X and Y and to transform the original image by use of the field for transformation.

The processing at the Step S4-2 is performed to fit an image to be processed to the template created at the Step S14 as a model. The template to be used is created with high accuracy by using the DARTEL algorithm, and accordingly the shape thereof is sharp.

Thereby, each image to be processed shares the similar shape therebetween because they are fit in the shape in which there is no individual difference by spatial normalization processing. On the other hand, atrophy is reflected in local density, and accordingly it is possible to improve accuracy of the spatial normalization.

Image smoothing at the Step S5 is performed to the white matter image and the gray matter image that are spatial-normalized as above (hereinafter, also as "a normalized brain image").

The smoothing is performed by using the three dimensional Gaussian kernel, to improve the SN ratio of the normalized brain image above and to equalize the smoothness of a group of images of normal individuals to be used as the standard at the time of comparing and that of the normalized brain image. The FWHM (Full Width at Half Maximum) of a filter used for the smoothing is set to be substantially 8 mm.

Specifically, as explained in the patent document 1, three dimensional convolving (convolution) of a three dimensional brain image with a three dimensional Gaussian function is performed. The convolution can be performed by consecutive one dimensional convolving in each direction of x, y, and z. The smoothing is processed in this way, and accordingly it is possible to reduce an individual difference that remains in an unfit state even through the spatial normalization processing.

FIG. 13 illustrates resultant images of spatial-processing at the Step S4 followed smoothing at the Step S5, with respect to the white matter image and the gray matter image separated at the Step S3.

Through the processing at the Step S4, information about the volume of the brain is reserved. Accordingly, before performing next correction of a concentration value, a value of integral of the whole image or regions of interest (ROI), which will be described later, can be measured as its volume to utilize it as diagnosis assistance information with respect to the resultant processed images of white matter and gray matter.

In order to fit voxel values in the whole brain to a distribution of voxel values in a group of images of normal individuals which is used as the standard at the time of comparing, correction of a concentration value to correct the voxel values in the whole brain in the normalized brain images that has been smoothed as above is performed (omitted in the drawings).

Thereafter, the statistical comparison at the Step S6 is performed. In the statistical comparison, a comparison test is performed between the MRI brain image of gray matter (white matter) of the subject, which has been normalized through the Steps S1 to S5 and a group of MRI brain images of normal individuals, which is collected beforehand and stored in the database unit 30 as the normal brain image database 36. It is desired that the group of images of normal individuals to be used is configured by images from individuals whose age is close to the subject's.

Figure 14:
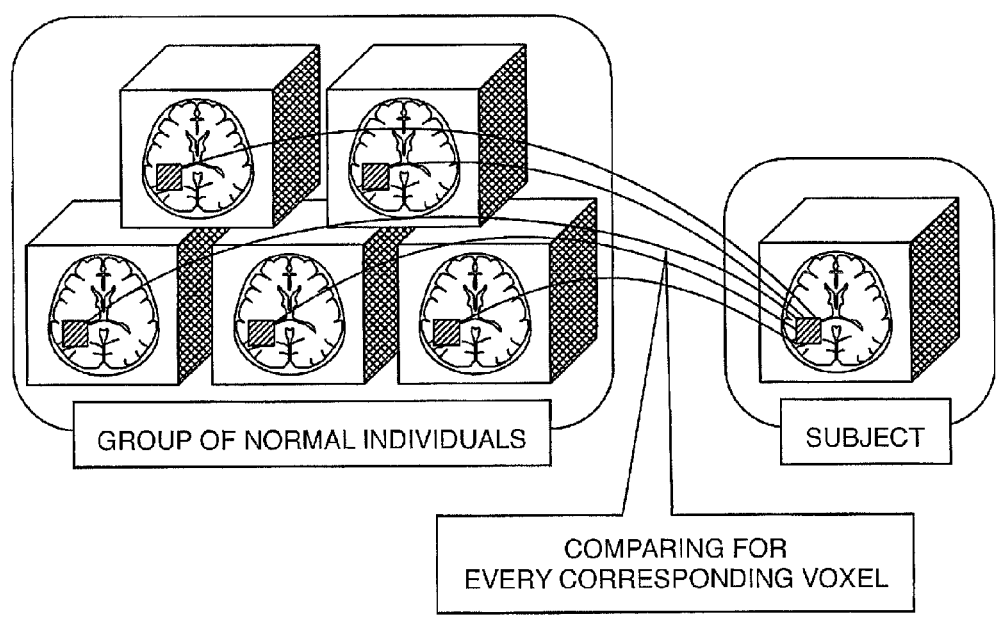
FIG. 14 is a conceptual diagram illustrating the features of comparison test for every voxel.

Specifically, as illustrated in the conceptual view in FIG. 14, the test for comparing the image of the subject with the group of images of normal individuals which includes the N number of images (N is the total number of images of normal individuals) for each voxel is performed (comparison test of the ratio 1:N) to detect a voxel that includes a statistically significant difference (that is estimated as being abnormal).

Firstly, Z-score that is represented by the following equations is calculated for every voxel respectively.

[Equation 1]

$$Z = \frac{\bar{x} - x}{\sigma} \quad (1)$$

Where,
x represents a value of a voxel of an image of a subject,
$\bar{x}$ represents an average of values of the corresponding voxels of a group of normal individuals, and
σ represents a standard deviation of values of the corresponding voxels of a group of normal individuals.

As indicated above, the Z-score is a value obtained by scaling, by the standard deviation, a difference between a value of a voxel of an image of the subject and an average of values of the corresponding voxels in the group of images of normal individuals, and represents the degree of relative decrease in the volume of gray matter (white matter).

Next, an appropriate critical value Z' is set, and a voxel of which the Z-score is greater than Z', that is, $$Z' \geq Z \quad (2)$$

is obtained and is set as the voxel that includes a statistically significant difference. As the critical value, it is used that Z'=2, from which an abnormality can be estimated with more than a 95% possibility. Furthermore, as a method for identifying a critical value that includes all regions of which the volume becomes less than that of normal individuals, the following equation is used as well.

$$O < Z' \quad (3)$$

The normal brain image database 36 used at the Step S6 is created similarly through a sequential process from the Steps S2 to S5, that is, spatial position adjustment, tissue separation processing of gray matter (white matter), spatial normalization, and smoothing processing, respectively, to the group of images of normal individuals collected beforehand, and stored the results within.

In addition, in the medical image processing device according to the present invention, these collected images of normal individuals are classified by age groups, for example, in intervals of five years or ten years, and an average value and a standard deviation calculated by each group are stored in a memory device so that a test by use of the Z-score can be performed.

Furthermore, comparison can be performed by use of images of normal individuals whose age is in a certain group of age range that is set so that the age of the subject becomes the center of the group. For example, if the subject is 76 years old, images of normal individuals whose age is between 74 to 78 years old, may be used so that the subject's age becomes the center of the range of normal individuals to compare (this case the range is set 5 years).

When using the Z-score like the above, it is enough to prepare the average value and the standard deviation for every voxel, and accordingly there is an advantage that it is not necessary to store image data itself after creation of data.

After statistical comparison of the normalized brain image of the subject is performed in the way described above, analysis by using ROI at the Step S7 is performed.

This is a method for setting regions of interest (ROI) in a predetermined size on an image (for example, see the non-patent document 5) to determine if abnormality exists in a brain image. A comparison is performed by setting a predetermined-sized ROI on a specific region that is focused on as relating to a specific disease.

The analysis method is performed as follows. As s explained in the patent document 1, in order to obtain degree of contracting a disease, a ROI (disease specific ROI) is applied with respect to those voxels having attributes such as position in coordinates and Z-sore (evaluation value) on which significant differences were found by the statistical processing. The analysis has the following two features.

(1) Preparing ROI (disease specific ROI) 38 for every disease such as Alzheimer's disease as normalized image data, then applying each ROI to which possible disease regarding subject's symptoms corresponds for subject's brain image, a diagnosis is obtained by comparing each significance in terms of Z-score brought from ROI thereof.

(2) Not only diagnosing the disease by the Z-score in the ROI, but also comparison between a Z-score map of the whole brain without the ROI and a Z-score map of within the ROI can be performed. The objective is to see the degree of atrophy in the region of interest in relation to that of the whole brain.

Figure 15:
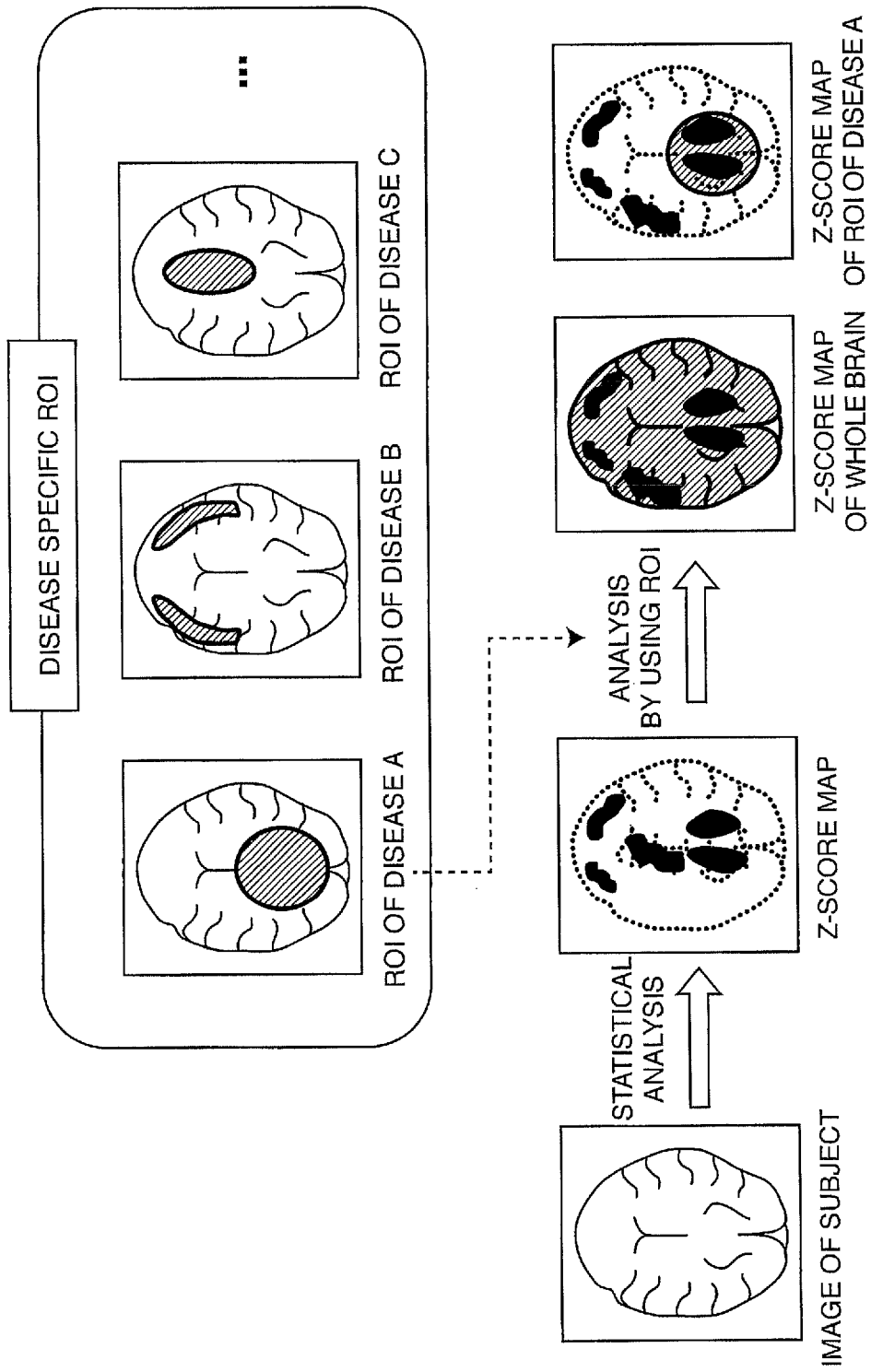
FIG. 15 is a conceptual diagram illustrating the features of analysis by ROI.

As illustrated in the conceptual view in FIG. 15, for example of the case where the specific ROI for each disease of A, B, and C, a method for diagnosing whether a subject is affected with the specific disease A will be described. Each ROI to be applied in the method will be described later.

With respect to the Z-score map of the subject which is obtained by the statistical comparison at the Step S6, the following five parameters are calculated by using the ROI that corresponds to the disease A, according to the Equations (2) and (3) mentioned above.

P1=the total of the Z-scores of the voxels in the ROI, which satisfy the Equation (3)/the number of voxels in the ROI, which satisfy the Equation (3)

P2=the number of voxels in the whole brain, which satisfy the Equation (2)/the number of voxels in the whole brain P3=the number of voxels in the ROI, which satisfy the Equation (2)/the number of voxels in the ROI

P4=P3/P2

P5=the maximum Z-score in all the voxels in the ROI

With respect to the five parameters of P1 to P5, characteristics of a group of patients who are affected with the disease A are obtained beforehand, and when a value of the parameter of the subject fits the characteristics, it is determined that the subject is affected with the disease A.

For example, threshold values (disease state discriminating values) which identify the disease A are set with respect to the five parameters, and when a value of the parameter which is obtained from an image of the subject exceeds the threshold values, it is determined that the subject is affected with the disease A. That is, in the case where the threshold values of each disease state discrimination according to the P1 to P5 are respectively set as thP1 to thP5, when at least one of the P1>thP1, P2>thP2, P3>thP3, P4>thP4, and P5>thP5 is satisfied, it is determined that the subject is affected with the disease A. Specifically, for example, it may be determined by only focusing on one parameter such as P1, or by referring to a part of P1 to P5 or all of them as necessary.

Furthermore, other than the parameters P1 to P5 mentioned above, values only at the right hemisphere or values only at the left hemisphere can be obtained so that they are added as parameters to the five parameters. In addition, for the values of the right hemisphere and those of the left hemisphere, the ratio between the left and right values which is obtained by the Equation (4) or the difference between the left and right values which is obtained by the Equation (5) can be added to the parameters.

$$\text{Ratio between the left and right values} = (R-L)/(R+L) * 200 \quad (4)$$

$$\text{Difference between the left and right values} = R-L \quad (5)$$

Where the value at the right hemisphere is set as R and the value at the left hemisphere is set as L.

Next, as a method for creating the ROI (disease specific ROI) that is set for each disease is described below.

Figure 16:
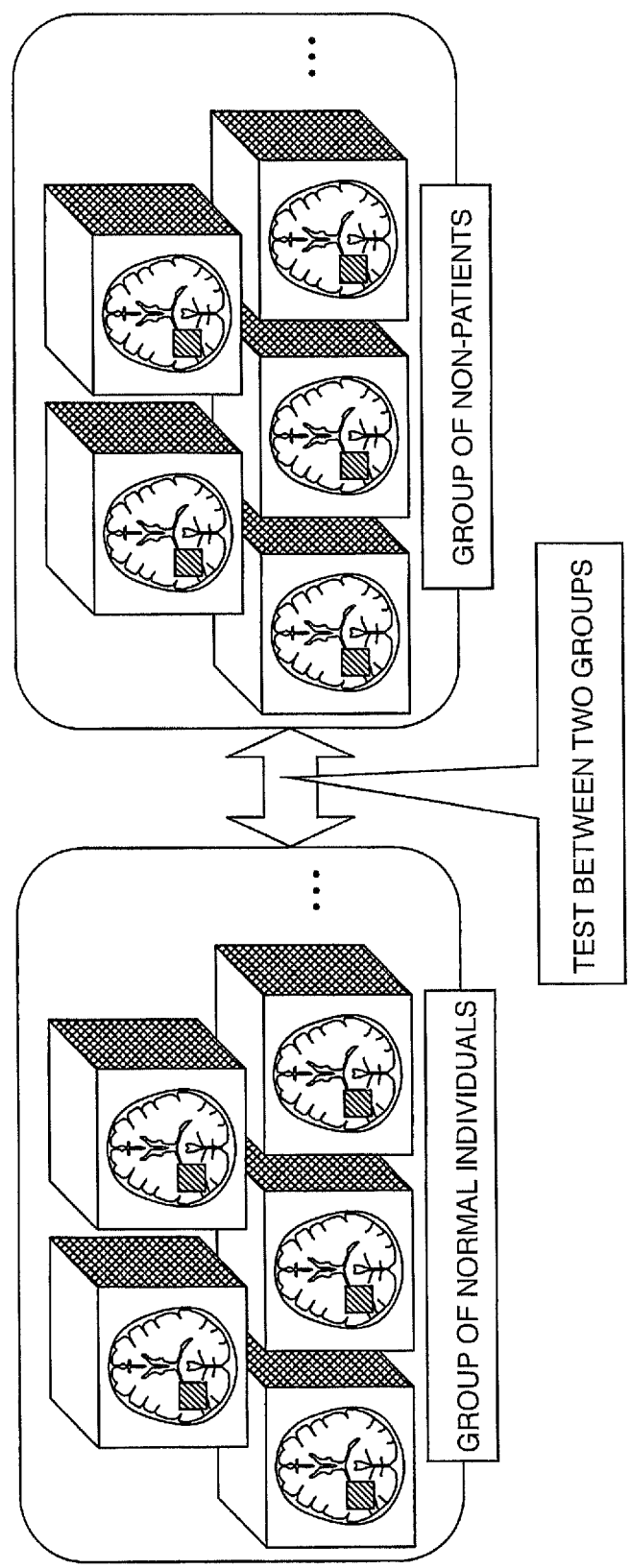
FIG. 16 is a conceptual diagram illustrating the features at the time of creating ROI.

ROI is determined based on statistical processing as follows. For example, in order to determine the ROI of the specific disease A, as illustrated in the conceptual view in FIG. 16, a two-sample t-test as a statistical test is performed to find a significant difference between the two groups, such as an MRI image group of patients with the disease A (patients image group) and an image group of the other individuals. A voxel that is found to have a significant difference by the test is identified as the characteristic voxel of the specific disease, and a set of the coordinates thereof is determined as the ROI that corresponds to the specific disease.

Disease state discriminating values (threshold values) are determined by general ROC (Receiver Operating Characteristic) analysis regarding the disease. The ROC analysis is a general method for measurably analyzing the capability for detecting the disease with respect of a certain test method.

As an example of the above, when identifying the presence of the disease based on the parameter P1 and the threshold value thP1, a method for obtaining the threshold value thP1 is described below.

A test is configured such that, in the case where P1>thP1 is satisfied, it is found positive and in the case where P1≤thP1 is satisfied, it is found negative. By examining a number of combinations of a positive or negative test result and the actual presence of the disease, each value of TP (True Positive), FP (False Positive), FN (False Negative), and TN (True Negative) is obtained such as illustrated in a chart in FIG. 17. Furthermore, the true positive fraction (TPF: the ratio of the case where a patient is correctly identified as a patient) and the false positive fraction (FPF: the ratio of the case where a normal individual is incorrectly identified as a patient) are represented by the values above as follows.

$$TPF=TP/(TP+FN)$$

$$FPF=FP/(FP+TN)$$

Figure 18:
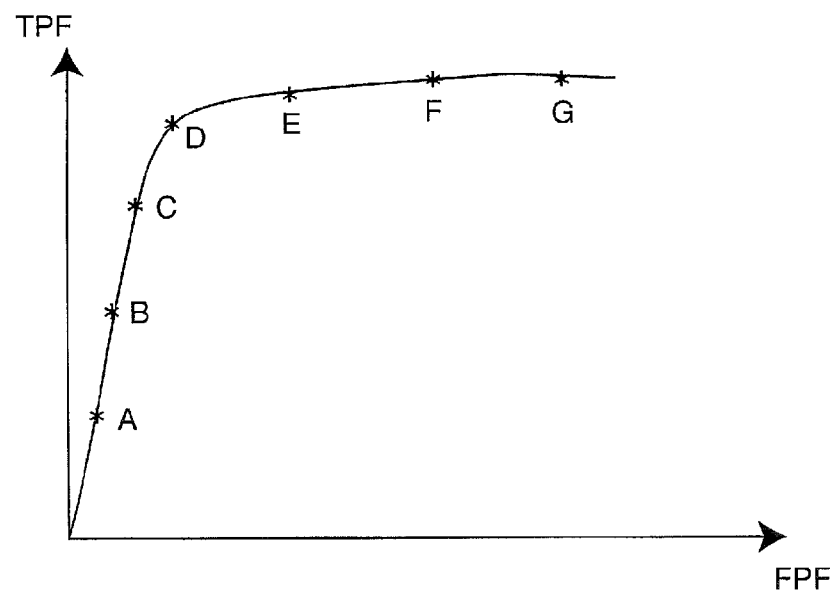
FIG. 18 is a diagram illustrating an example illustrating an ROC curve.

One pair of (TPF, FPF) is obtained in the specific thP1, and the pairs of (TPF, FPF) obtained by changing the threshold values in various ways are plotted to form the ROC curve illustrated in FIG. 18.

It is desired that the test proves the high TPF and low FPF, and the most top-left point in the ROC curve corresponds thereto. For example, in FIG. 18, it is recommended to use the threshold that corresponds to the point D.

Figure 19:
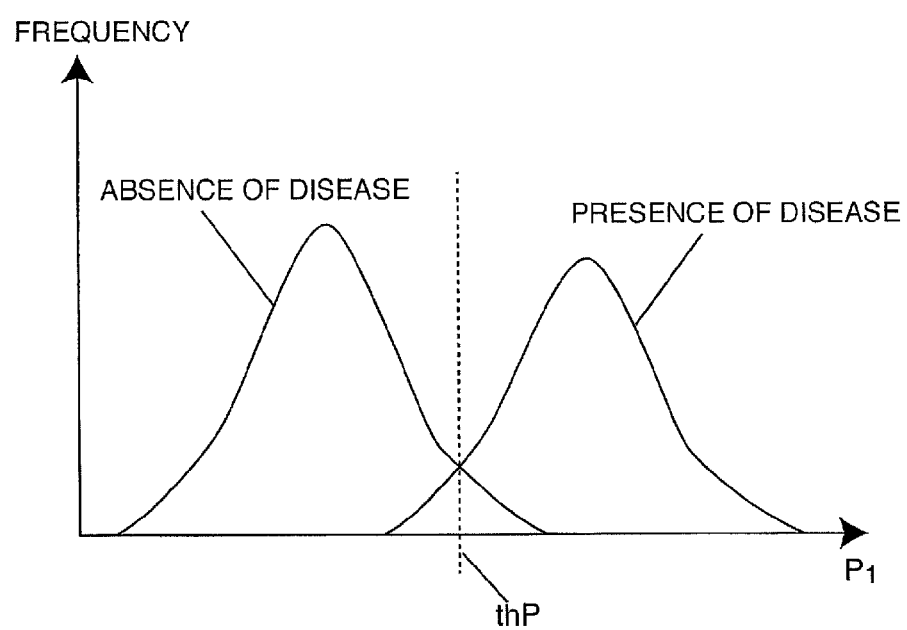
FIG. 19 is a diagram illustrating an identification method by one parameter.

When the above is considered from an aspect of the parameters and the presence of disease and is explained in the case where one parameter is used for reasons of expediency, as illustrated in FIG. 19, a border line that correctly divides (without errors) the distributions of having the disease and not having the disease corresponds to the threshold value that is obtained herein.

EXAMPLE

T1-weighted MRI brain images of a subject and those of a group of normal individuals are imaged by an MRI device, and each image is stored as DICOM format files. The DICOM format is a generally used image format for a medical image including both a header part and an image data part in a file, and is capable of storing therein a parameter and diagnostic information at the time of imaging. Normally, one piece of the DICOM image file includes information about one piece of slice image, and a three dimensional brain image is expressed by a plurality of the DICOM images. The DICOM images are stored in a DICOM server and can be pulled up as necessary.

Three dimensional information about the whole brain is expressed by a plurality of DICOM image files. And the DICOM image file is converted to the Analyze format that is a format in which either header parts of the DICOM files or image data parts thereof are joined. The Analyze format can configure the whole brain for one individual by two types of files such as a header part file and an image data file.

The SPM (Statistical Parametric Mapping) etc. is known as the one in which a tool for image processing of a brain image is implemented on software. The SPM is applied to image processing described below of the present example.

Under the conditions described above, each processing at the Steps S1 to S7 in FIG. 2 is performed to an MRI image obtained from a subject.

As a template to be used for extracting white matter and gray matter, the one which is created by the ICBM (International Consortium for Brain Mapping) is used. This template calculates the prior occurrence (existence) probability of white matter, gray matter, and cerebrospinal fluid from brain images of a number of normal individuals, and the size of one voxel thereof is 2 mm square.

The Steps S11 to S14 as the preparation processing and the Steps S1 to S5 as the diagnostic-assistance-information creation processing are performed by using 61 examples of a group of patients with Alzheimer's dementia and 82 examples of a group of normal aged individuals.

The ROC analysis by using the P1 obtained at the Step S7 is performed to the processing result of the gray matter image to obtain the AUC (Area Under the Curve) that represents the area under the ROC curve. Consequently, the result is 0.876 by the method according to the patent document 1, and the result is 0.943 by the method according to the present invention. Furthermore, as a result of comparing diagnostic accuracy between the method according to the patent document 1 and the method according to the present invention, it is revealed that the diagnostic accuracy to identify the individual with the Alzheimer's dementia from normal aged individuals by the method according to the present invention is about 5% higher than that by the method according to the patent document 1. The results above show that the method according to the present invention is effective to the diagnosis of Alzheimer's dementia.

Furthermore, it is possible to realize spatial normalization of a white matter image, which has not been realized so far. By evaluating both gray matter lesion and white matter lesion, for example, the accuracy to identify Alzheimer's dementia from vascular dementia can be improved.

As described above, according to the present embodiment, upon input of an MRI image of a subject, white matter image presenting white matter that is extracted from the input MRI image by tissue separation is created, and then the created white matter image is spatial-normalized based on a white matter template that has been stored beforehand to create the normalized white matter image. When statistically comparing white matter of a subject and white matter of a plurality of normal individuals based on the created normalized white matter image, the white matter template is created by spatial normalization of white matter images of a plurality of normal individuals, which uses the DARTEL algorithm, and accordingly it is possible to create a highly-accurate white matter template. Therefore, it becomes possible to objectively assist in diagnosis of a specific disease regarding white matter, which has not been realized so far.

Similarly, a gray matter image presenting gray matter that is extracted from the input MRI image by tissue separation is also created, and then the created gray-matter image is spatial-normalized based on a gray matter template that has been stored beforehand to create the normalized gray matter image. Gray matter of a subject and gray matter of a plurality of normal individuals is statistically compared based on the created normalized gray matter image, and accordingly it is possible to create a gray matter template as well with more accuracy ever before in the same method. Therefore, it becomes possible to objectively assist in diagnosis of a specific disease regarding great matter with more accuracy.

Furthermore, according to the present embodiment, white matter and gray matter templates are created and stored by a participants' age and sex, and accordingly spatial normalization can be performed by using an appropriate template in accordance with a subject's age and sex. Therefore, it is possible to realize assistance in diagnosis with more accuracy.

That is, according to the present embodiment, the DARTEL algorithm is used for spatial normalization, and accordingly it becomes possible to improve the accuracy of spatial normalization regarding white matter, although the spatial normalization has been performed only for gray matter so far. In addition, the templates that are created by participants' age and sex are stored in the database unit 30 so that they are appropriately selected and applied to an input image, and accordingly the influence by a subject's age and sex can be considered.

The present invention is specifically described above, however, the present invention is not limited by the embodiment above and various changes may be made without departing from the scope of the invention.

For example, the test method using the Z-score as an evaluation value is explained above, however, the present invention is not limited thereto and t-score that is used in other general tests can be used.

The preparation processing according to the present invention is not limited to the embodiment above, however, it can be applied to overall brain image to be subject to tissue separation. For example, it can be used as pre-processing of extraction of gray matter tissue performed with tissue separation, which is explained in the patent document 1.

Furthermore, in the present embodiment above, the preparation processing (Steps S11 and S1) is configured to be performed prior to the spatial position adjustment (Steps S12 and S2) in both of the pre-processing and the basic processing, however, the preparation processing (Steps S11 and S1) can be performed after the spatial position adjustment (Steps S12 and S2). In such a case, when determining necessity of high-signal-value control, complicated processing for selecting slice images described above in the target slice selection processing at the Step S21 is not required because the spatial position is already adjusted, but it only requires to specify a portion of an upper part of the brain in which image element with high signal value is not considered to exist other than the region around the skull and the cerebral parenchyma. Specifically, it is enough to specify a range of order numbers of slice images from the top to be selected as target slices.

Furthermore, in the present embodiment, the preparation processing at the Step S1 and the diagnostic-assistance-information creation processing through the Steps S2 to S7 are configured to be performed successively in one medical image processing device, and the preparation processing at the Step S11 and the pre-processing through the Step S12 to S14 are configured to be performed successively in one medical image processing device. However, it can be configured such that only the preparation processing at the Steps S1 and S11 is performed in a medical image processing device, and the pre-processing and the diagnostic-assistance-information creation processing are performed with respect to the obtained image after being processed with the high-signal-value control by other device. In this case, when performing the spatial position adjustment (Steps S12 and S2) initially, it is configured such that only the preparation processing at the Steps S2 and S1 and Steps S12 and S11 is performed in the medical image processing device, and the pre-processing and the diagnostic-assistance-information creation processing are performed with respect to the obtained image after being processed with the high-signal-value control by other device.

DESCRIPTION OF NOTATIONS

10 User interface
20 Image and statistical processing unit
30 Database unit
32 White matter brain image template
34 Gray-matter brain image template
36 Normal brain image database
38 Disease specific ROI

The invention claimed is:
1. A medical image processing device comprising:
a target slice selection unit that selects a slice image to be processed as a target slice from a brain image that is configured by a plurality of slice images;
a cerebral parenchyma measurement unit that performs measurement processing to determine an effective maximum value in the cerebral parenchyma, which is an effective maximum value of signal values of image elements in the cerebral parenchyma;

a brain image measurement unit that performs measurement processing to determine an effective maximum value of signal values of image elements in the whole brain image;

a skull measurement unit that performs measurement processing to determine a peak average value around the skull, which is an average of signal values of image elements that are at peaks in a region around the skull;

a control processing determination unit that determines necessity of high-signal-value-control processing based on the effective maximum value in the cerebral parenchyma, the effective maximum value in the whole brain image, and the peak average value around the skull; and a high-signal-value-control processing unit that performs the high-signal-value-control processing with respect to the brain image when the control processing determination unit determines that the high-signal-value-control processing is necessary.

2. The medical image processing device according to claim 1, wherein the control processing determination unit performs:

a skull region determination to determine whether the peak average value around the skull is higher at a constant rate than the effective maximum value in the cerebral parenchyma; and a whole image determination to determine whether the signal values in the whole image are higher at a constant rate than the effective maximum value in the cerebral parenchyma, and a judgment is obtained such that either the skull region determination or the whole image determination satisfies the condition, the high-signal-value-control processing be necessary.

3. The medical image processing device according to claim 1, wherein, with respect to each slice image, the target slice selection unit sets a predetermined line segment within an image, obtains a length between image elements of which distance therebetween is the largest among image elements that are on the line segment with signal values higher than a predetermined value, and selects a target slice, in which said length between image elements is longer than the length determined by a predetermined ration based on the maximum said length among all the slice images.

4. The medical image processing device according to claim 1, wherein, with respect to the selected each target slice, the cerebral parenchyma measurement unit sets predetermined number of line segments that cross over a center part of a brain, divides, for every line segment, the signal value distribution of image elements on one of the line segment into a predetermined number of regions, and acquires a histogram of signal values in the cerebral parenchyma region, the cerebral parenchyma region corresponding central part of each line segment, consisting of certain number of the regions, then calculates the maximum of all the signal values left after excluded upper predetermined image elements to determine an effective value of the cerebral parenchyma.

5. The medical image processing device according to claim 1, wherein, the brain image measurement unit acquires a histogram of signal values of image element in a whole target slice, then calculates the maximum of all the signal values left after excluded upper predetermined image elements to determine an effective maximum value in a whole image.

6. The medical image processing device according to claim 1, wherein, with respect to the selected each target slice, the skull measurement unit sets a predetermined number of line segments that cross over a center part of a brain, divide, for every line segment, the signal value distribution of image elements on one of the line segment into a predetermined number of regions, and acquires a maximum value of signal values in the skull region, the skull region corresponding either end of each line segment, consisting of certain number of the regions, then calculates an average of the maximum value among all the line segments on all the target slices to determine an peak average value of the skull.

7. The medical image processing device according to claim 1, wherein, high-signal-value-control processing unit realizes the high-signal-value-control processing relatively by controlling in such a way that a signal value of an image element is unchanged if its signal value is lower than a predetermined value, a signal value of an image element is limited to the predetermined value if its signal value is equal to or higher than the predetermined value.

8. The medical image processing device according to claim 1, wherein, high-signal-value-control processing unit realizes the high-signal-value-control processing relatively by controlling in such a way that a signal value of an image element is unchanged if its signal value is lower than a predetermined value, a signal value of an image element is lowered than the original thereof if its signal value is equal to or higher than the predetermined value.

9. The medical image processing device according to claim 8, wherein, high-signal-value-control processing unit realizes the high-signal-value-control processing relatively by controlling in such a way that a signal value of an image element is unchanged if its signal value is lower than a predetermined value, a signal value of an image element is transformed by a linear function of which gradient equals to zero or is positive and smaller than 1.

10. A non-transitory computer-readable medium storing a computer-readable program that, when executed, performs the operations comprising:

selecting a slice image to be processed as a target slice from a brain image that is configured by a plurality of slice images;

performing measurement processing to determine an effective maximum value in the cerebral parenchyma, which is an effective maximum value of signal values of image elements in the cerebral parenchyma;

performing measurement processing to determine an effective maximum value of signal values of image elements in the whole brain image;

performing measurement processing to determine a peak average value around a skull, which is an average of signal values of image elements that are at peaks in a region around the skull;

determining necessity of high-signal-value-control processing based on the effective maximum value in the cerebral parenchyma, the effective maximum value in the whole brain image, and the peak average value around the skull; and performing the high-signal-value-control processing with respect to the brain image when the control processing determination unit determines that the high-signal-value-control processing is necessary.

* * * * *